(12) United States Patent
Wang et al.

(10) Patent No.: US 8,115,002 B2
(45) Date of Patent: Feb. 14, 2012

(54) PREPARATION OF SUBSTITUTED MORPHINAN-6-ONES AND SALTS AND INTERMEDIATES THEREOF

(75) Inventors: Peter X. Wang, Chesterfield, MO (US); Frank W. Moser, Arnold, MO (US); Gary L. Cantrell, Troy, IL (US); Christopher W. Grote, Webster Groves, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 435 days.

(21) Appl. No.: 12/441,397

(22) PCT Filed: Sep. 6, 2007

(86) PCT No.: PCT/US2007/019489
§ 371 (c)(1),
(2), (4) Date: Mar. 16, 2009

(87) PCT Pub. No.: WO2008/036172
PCT Pub. Date: Mar. 27, 2008

(65) Prior Publication Data
US 2010/0048906 A1 Feb. 25, 2010

Related U.S. Application Data

(60) Provisional application No. 60/845,956, filed on Sep. 20, 2006, provisional application No. 60/940,463, filed on May 29, 2007.

(51) Int. Cl.
*C07D 221/28* (2006.01)
(52) U.S. Cl. ........... 546/74; 546/146; 546/149; 546/148
(58) Field of Classification Search ............... 546/74, 546/146, 149
See application file for complete search history.

(56) References Cited

U.S. PATENT DOCUMENTS

| | | | |
|---|---|---|---|
| 3,101,339 A | 8/1963 | Zeile et al. | |
| 4,141,897 A | 2/1979 | Olofson et al. | |
| 4,176,186 A | 11/1979 | Goldberg et al. | |
| 4,322,426 A | 3/1982 | Hermann et al. | |
| 4,368,326 A | 1/1983 | Rice | |
| 4,410,700 A | 10/1983 | Rice | |
| 4,456,712 A | 6/1984 | Christie et al. | |
| 4,521,601 A | 6/1985 | Rice | |
| 4,535,157 A | 8/1985 | Meltzer et al. | |
| 4,556,172 A | 12/1985 | Sugawara et al. | |
| 4,556,712 A * | 12/1985 | Rice ............... | 546/149 |
| 4,613,668 A | 9/1986 | Rice | |
| 4,727,146 A | 2/1988 | Rice | |
| 4,794,186 A | 12/1988 | Oine et al. | |
| 4,952,730 A * | 8/1990 | Leuchs et al. ........... | 564/302 |
| 5,112,975 A | 5/1992 | Wallace | |
| 5,240,933 A | 8/1993 | Merz et al. | |
| 5,352,680 A | 10/1994 | Portoghese et al. | |
| 5,574,159 A | 11/1996 | Chang et al. | |
| 5,668,285 A | 9/1997 | Rice et al. | |
| 5,869,669 A | 2/1999 | Huang et al. | |
| 5,907,069 A | 5/1999 | Becnel et al. | |
| 5,922,876 A | 7/1999 | Huang et al. | |
| 5,948,788 A | 9/1999 | Huang et al. | |
| 5,952,495 A | 9/1999 | Huang et al. | |
| 5,981,474 A | 11/1999 | Manning et al. | |
| 6,008,354 A | 12/1999 | Huang et al. | |
| 6,008,355 A | 12/1999 | Huang et al. | |
| 6,013,796 A | 1/2000 | Huang et al. | |
| 6,136,817 A | 10/2000 | Schmidhammer | |
| 6,174,891 B1 | 1/2001 | Nagase et al. | |
| 6,365,742 B1 | 4/2002 | Mudryk et al. | |
| 2002/0128496 A1 * | 9/2002 | Chang et al. ............... | 549/445 |
| 2005/0182258 A1 | 8/2005 | Schmidhammer et al. | |
| 2007/0265293 A1 | 11/2007 | Boyd et al. | |
| 2008/0064712 A1 | 3/2008 | Schmidhammer et al. | |
| 2008/0146804 A1 | 6/2008 | Stumpf | |
| 2008/0207906 A1 | 8/2008 | Wang et al. | |
| 2009/0270624 A1 | 10/2009 | Weigl et al. | |

FOREIGN PATENT DOCUMENTS

| | | |
|---|---|---|
| EP | 0 028 959 | 1/1985 |
| ES | 2 121 554 | 11/1998 |
| PL | 124 001 | 7/1985 |
| WO | WO 01/55117 | 8/2001 |
| WO | WO 2004/029059 | 4/2004 |
| WO | WO 2004/043964 | 5/2004 |
| WO | WO 2006/127899 | 11/2006 |

OTHER PUBLICATIONS

Still et al. J. Org. Chem. 1978, 43, 2923-2925.*
Rice, "Synthetic Opium Alkaloids and Derivatives. A Short Total Synthesis . . . ", J. Or. Chem.., 1980, 45, pp. 3135-3137.
Beyerman et al., Recl. Trav. Chim. Pays-Bas., 1976, 95, 184.
Degraw et al., J. Het. Chem., Jun. 1974, 363.
Amaravathi et al., "Oxidation of 1-benzyl-3,4-dihydroisoquinolines using active manganese dioxide," Indian Journal of Chemistry, Section B: Organic Chemistry Including Medicinal Chemistry (1983), 22B(12), 1246-7.
Andreu et al., "An efficient method for the preparation of antitumoral α-keto-imines benzyldihydroisoquinolines by selective benzylic oxidation with C/Pd in acetonitrile," Tetrahedron Letters (2002), 43(5), 757-759.
Archer et al., "1-Acetamido-17-carbomethoxydihydrothebainone," Journal of Heterocyclic Chemistry (1981), 18(2), 357-61.
Baxendale et al., "Enantioselective synthesis of the tetrahydrobenzylisoquinoline alkaloid (−)-norarmepavine using polymer supported reagents," Heterocycles (2003), 60(12), 2707-2715.
Benosman et al., "Synthesis of isoquinolines isolated fro *Aniba canelilla*", Comptes Rendus de I'Academie des Sciences, Serie II:Mecanique, Physique, Chimie, Sciences de la Terre et de l'Univers, 19983, 316(4), pp. 465-468 (French Language), 1983.
Bentley et al., The Reduction of Thebaine and Dihydrothebaine by Sodium and Ammonia, Journal of the Chemical Society, Abstracts (1952), pp. 958-966.

(Continued)

*Primary Examiner* — Joseph Kosack
*Assistant Examiner* — Matthew Coughlin

(57) ABSTRACT

The present invention is directed to processes for the synthesis of morphinan-6-ones and salts, intermediates, and analogs thereof.

31 Claims, No Drawings

OTHER PUBLICATIONS

Bermejo et al., "Syntheses and antitumor targeting G1 phase of the cell cycle . . . ", Journal of Medicinal Chemistry, 2002, 45(23), pp. 5058-5068.
Bhakuni et al., "Sunthesis of (±)-12-amino derivatives of scoulerine, . . . ", Indian Journal of Chemistry, Section B: Organic chemistry Including Medicinal Chemistry, 1985, 24B(6), pp. 596-601.
Bhakuni et al., "Studies on mannich reaction of 1-benzyltetrahydroisoquinolines", Journal of the Indian Chemical Society, 1988, 65(6), pp. 417-421.
Bjorklund et al., "Cryptic Stereochemistry of Berberine alkaloid biosynthesis", Journal of the American Chemical Society, 1995, 117(5), pp. 1533-1545.
Boehme et al., "Analogs of M4 selective synthetic muscarinic receptor antagonists: . . . ", Medicinal Chemistry Research, 2002, 11(8), pp. 423-433.
Bognar et al., "Selective Quaternization in the Morphine Series", Tetrahedron Letters, 1964, No. 39, pp. 2867-2871.
Cave et al., "Alkaloids of cryptocarya phyllostemon", Australian Journal of Chemistry, 1989, 42(12), pp. 2243-2263.
Chackalamannil et al., "The synthesis of erythro- and threo-N-methyl-7-hydroxy-1,2,9,10-tetramethoxyaporphine", Tetrahedron Letters, 1980, 21(21), pp. 2029-2032.
Chazerain, "1-Benzoylisoquinolines and their transformation into 1-phenyl-3-benzazepines", Ann. Chim. (Paris), 1963, 8, pp. 255-284.
Cho et al., "Synthesis of 6,7-dimethoxy-1-halobenzyl-1,2,3,4-tetrahydroisoquinolines," Journal of Heterocyclic Chemistry (1999), 36(5), 1151-1156.
Chrzanowska et al., "Asymmetric synthesis of isoquinoline alkaloids," Chemical Reviews (2004), 104, 3341-3370.
Chrzanowska et al., "Synthesis of (S)-(−)- and (R)-(+)-O-methylbharatamine using a diastereoselective Pomeranz-Fritsch-Bobbitt methodology," Tetrahedron: Asymmetry (2005), 16(17), 2954-2958.
Coutts et al., "The enzymatic oxidation of phenolic tetrahydroisoquinoline-1-carboxylic acids," Journal of the Chemical Society, Perkin Transactions 1: Organic and Bio-Organic Chemistry (1972-1999) (1979), (11), 2744-50.
Crooks et al., "Opiate receptor binding properties of morphine-, dihydromorphine-, and codeine 6-0-sulfate ester congeners", Bioorganic & Medicinal Chemistry Letters, 16, 2006, pp. 4291-4295.
Czarnocki, "Enantioselective syntheis of (R)-(−)-calycotomine and (S)-(−)-xylopinine from D-ribonolactone" , Journal of Chemical Research, Synopses, 1992, 10, pp. 334-335.
Czarnocki et al., "Asymmetric synthesis of isoquinoline alkaloids. (R)- and (S)-2-(ethoxycarbonyl)-1-formyl-6, . . . ", bulletin des Societes Chimiques Belges, 1986, 95(9-10), pp. 749-770.
Davis et al., "Synthesis of the orotoberberine alkaloid (S)-(−)-xylopinine using enantiopure sulfinimines", Journal of Organic Chemistry, 2002, 67(4), pp. 1290-1296.
Fry et al., Mannich Derivatives of Analgesic Agents, Journal of Organic Chemistry (1959), 24, pp. 116-117.
Funke et al., A $^1$H and $^{13}$C Nuclear Magnetic Resonance Study of Three Quaternary Salts of Naloxone and Oxymorphone, J. Chem. Soc. Perkin Trans. (1986) 2, pp. 735-738.
Giger et al., Synthesis and Reactions of the diels-Alder Adduct of Thebaine with 4-phenyl-1,2,4-triazoline-3,5-dione, Tetrahedron (1973), 29(16), pp. 2387-2391.
Gupta et al., "Synthetic photochemistry: Synthesis of Iiriodenine," Indian Journal of Chemistry, Section B: Organic Chemistry Including Medicinal Chemistry (1983), 22B(5), 429-31.
Hanaoka et al., "Chemical transformation of protoberberines. VIII. A novel synthesis of (±)-fumaricine and a formal synthesis of (±)-alpinigenine," Chemical and Pharmaceutical Bulletin (1985), 33(6), 2273-80.
Hirai et al., "A new preparation of an ochotensin-type isoquinoline by photolysis," Heterocycles (1984), 22(6), 1359-62.
Hu et al., "Photosynthesis of tetrahydroprotoberberines with electron-withdrawing groups on ring D," Chinese Chemical Letters (1998), 9(8), 707-710.

Iorio et al., "Diastereoisomeric Quaternary Morphinium Salts: Synthesis, Stereochemistry and Analgesic Properties", European Journal of Medicinal Chemistry, 1984, 19(1), pp. 11-16.
Kaldor et al., "Stereocontrolled synthesis of cis-dibenzoquinolizine chlorofumarates: curare-like agents of ultrashort duration," Journal of Organic Chemistry (2001), 66(10), 3495-3501.
Kametani et al., "Studies on the syntheses of heterocyclic compounds. DCXCII. A novel synthetic route to phthalideisoquinoline and spirobenzylisoquinoline type alkaloids," Chemical and Pharmaceutical Bulletin (1977), 25(2), 321-6.
Kametani et al., "Studies on the syntheses of heterocyclic compounds. DCXCII. A stereoselective Total Synthesis of (±)-Ophiocarpine; a Simple Route to 13-Hydroxyberbines", JCS Perkin I, 1977, pp. 376-382.
Kametani et al., "Studies on the syntheses of heterocyclic compounds. DCXCIII. A total synthesis of atheroline by photolysis," Tetrahedron (1977), 33(9), 1069-71.
Kametani et al., "Synthesis of oxoaporphine by photolysis. Total synthesis of atheroline," Heterocycles (1975), 3(10), 821-5.
Kapadia et al., "Facile oxidative formation of O-methylvelucryptine during synthesis of dl-O-methylarmepavine," Indian Journal of Pharmaceutical Sciences (1992), 54(6), 227-33.
Kessar et al., "Synthetic Photochemistry: Synthesis of (±)-oliveridine," Indian Journal of Chemistry, Section B: Organic Chemistry Including Medicinal Chemistry (1983), 22B(4), 321-4.
Koczka et al., Selective Quaternization of Compounds with Morphine Skeleton, Acta. Chim. Acad. Sci. Hung. (1967), 51(4), pp. 393-402.
Kunitomo et al., "Synthesis of a few trimethoxyoxoaporphines," Yakugaku Zasshi (1979), 99(1), 102-5. (Japanese language).
Kuo et al., "Antiplatelet activity of benzylisoquinoline derivatives oxidized by cerium (IV) ammonium nitrate," Bioorganic and Medicinal Chemistry Letters (2003), 13(16), 2789-2793.
Lebceuf et al., "Velucryptine, A new isoquinoline alkaloid from cryptocarya velutinosa," Journal of Natural Products (1989), 52(3), 516-21.
Lenz et al., "Lead tetraacetate mediated oxidation of the enamides derived from 1-benzyl-3,4-dihydroisoquinolines," Journal of Organic Chemistry (1988), 53(6), 1176-83.
Lenz et al., "Synthesis of the novel isoquinoline enamide alkaloid polycarpine," Journal of Heterocyclic Chemistry (1981), 18(4), 691-3.
Lopez et al., Photoxidation of Thebaine. A Route to 14-Hydroxymorphinones and Hydrodibenzofuran Analogs of Methadone, Tetrahedron Letters (1994), 35(31), pp. 5727-5730.
Lopez et al., The [4+2] Addition of Singlet Oxygen to Thebaine: New Access to Highly Functionalized Morphine Derivatives via Opioid Endoperoxides, J. Org. Chem. (2000), 65(15), pp. 4671-4678.
Manoharan et al., "Convenient Method for Replacement of Tertiary N-Methyl by Other Alkyl Groups: Application to Morphine Alkaloids", Indian Journal of Chemistry, 1984, vol. 19, No. 1, pp. 5-11.
Manoharan et al., Stereoselectivity in Quaternization of Thebaine: 270 MHz PMR Spectroscopic Studies, Indian Journal of Chemistry, Section B: Organic Chemistry Including Medicinal chemistry (1987), 26B(2), pp. 140-142.
Markaryan et al., "Isoquinoline derivatives. XI. Synthesis and pharmacological activity of 1-arylalkyl-4-spirocyclohexane-6,7-dimethoxy-1,2,3,4-tetrahydroisoquinolines and some of their derivatives," Armyanskii Khimicheskii Zhurnal (1975), 28(10), 829-35. (Russian language).
Martin et al., "Oxidation of imines by selenium dioxide," Zeitschrift fuer Naturforschung, Teil B: Anorganische Chemie, Organische Chemie (1986), 41B(10), 1260-4.
Martin et al., "Regiospecific oxidation of substituted 1-benzyl-3,4-dihydroisoquinolines using singlet oxygen," Tetrahedron Letters (1980), 21(27), 2613-16.
Martin et al., "Synthesis and photooxygenation of some substituted 1-benzyl-3,4-dihydroisoquinolines. Mechanism of enamine photooxygenation," Helvetica Chimica Acta (1982), 65(3), 762-74.
McMahon et al., "Rearrangement of 1-(α-hydroxybenzyl)-1,2,3,4-tetrahydroisoquinolines to 1-phenyl-2,3,4,5-tetrahydro-1H-3-benzazepines," Journal of the Chemical Society, Perkin Transactions 1: Organic and Bio-Organic Chemistry (1972-1999) (1982), (9), 2163-7.
Memetzidis et al., "Synthesis of aromatic chloroberbines," Heterocycles (1990), 31(2), 341-51.

Meuzelaar et al., "Chemistry of opium alkaloids. Part 45. Improvements in the total synthesis of morphine," European Journal of Organic Chemistry (1999), 2315-2321.

Meyers et al., "Asymmetric synthesis of isoquinoline alkaloids", Tetrahedron, 1987, 43(21), pp. 5095-5108.

Meyers et al., "High enantioselective alkyation of tetrahydroisoquinolines with a chiral valinol derivative . . . ", Angewandte Chemie, 1984, 16(6), pp. 448-449.

Miller et al., "Synthesis and biological evaluation of fragmented derivatives of tetrahydroisoquinolines. 2. Trimetoquinol studies", Journal of Medicinal Chemistry, 1975, 18(5), pp. 454-457.

Mujahidin et al., "Enantioselective synthesis of (+)-(S)-laudanosine and (−)-(S)-xylopinine," European Journal of Organic Chemistry (2005), 2689-2693.

Musich et al., Reaction of O-methyl-N, $N^1$-Diisopropylisourea with Amino Acids and Amines, Journal of Organic Chemistry (1977), 42(1), pp. 139-141.

Nagata et al., Synthetic Studies on Isoquinoline Alkaloids. I.* An Efficient Synthesis of 9,10-Substituted Protoberberine Alkaloids 1, Chem. Pharm. Bull., 23(11), 1975, pp. 2867-2877.

Naito et al., "Asymmetric synthesis of dibenzo[a,g]quinolizines related to protoberberine alkaloids," Heterocycles (1983), 20(5), 779-82.

Naito et al., "Reductive photocyclization of enamides and its application to alkaloid synthesis", Kobe Women's Coll. Pharm., Tennen Yuki Kagobutsu Toronkai Koen Yoshishu, 24th, 1981, pp. 460-465.

Naito et al., "Reductive photocyclization of enamide in the presence of a chriral metal hydride complex . . . ", Kobe Women's Coll. Pharm., Heterocycles, 1981, 16(7), pp. 1141-1143.

Ninan et al., "An Improved Synthesis of Noroxymorphone", Tetrahedron, 48(32), 1992, pp. 6709-6716.

Orito et al., "Aryl radical cyclizations of 1-(2'-Bromobenzyl)isoquinolines with AIBN-Bu3SnH: Formation of aporphines and Indolo[2,1-a]isoquinolines," Organic Letters (2000), 2(3), 307-310.

Orito et al., "New synthesis of phthalideisoquinoline alkaloids via a stereoselective hydride reduction of 1-(2'-bromobenzoyl)-3,4-dihydroisoquinoline methiodide, followed by palladium-catalyzed carbonylation aided by chlorotrimethylsilane," Synlett (1994), (4), 245-6.

Orito et al., "Synthesis of (±)-norcoralydine and (±)-tetrahydropalmatine," Organic Preparations and Procedures International (1989), 21(3), 309-14.

Orito et al., "Synthesis of phthalideisoquinoline and protoberberine alkaloids and indolo [2,1-a] isoquinolines in a divergent route involving palladium(0)-catalyzed carbonylation," Journal of Organic Chemistry (1999), 64(18), 6583-6596.

Otto et al., Selection and Amplification of Hosts from Dynamic combinatorial Libraries of Macrocyclic Disulfides, Science (Washington, DC, United States) (2002), 297(5581), pp. 590-593 & Supporting Online Material.

Rozwadowska et al., "Mammalian alkaloids: O-methylation of (S)- and (R)-dideoxynorlaudanosoline-1-carboxylic acid by catechol O-methyltransferase and identification of a yellow pigment obtained at physiological pH," Helvetica Chimica Acta (1988), 71(7), 1598-607.

Schultz et al., Thebaine Cyclopropanation, Russian Journal of Organic chemistry (Translation of Zhurnal Organicheskoi Khimii) (2003), 39(8), pp. 1083-1088.

Seki, Isao, Studies on the Morphine Alkaloids and its Related Compounds. XIV. Preparation of 6-Amino-hydrophenanthrene Compounds from Hofmann Degradation Products of the Morphine Alkaloids, Chemical & Pharmaceutical Bulletin (1966), 14(5), pp. 453-461.

Shklyaev et al., "A new approach to synthesis of 3,3-dialkyl-3,4-dihydroisoquinoline derivatives," Heteroatom Chemistry (2004), 15(7), 486-493.

Shults et al., Tranformations of Quaternary Tetrahydrothebaine Sulfones, Zh. Org. Khim. (1993), 29(6), pp. 1149-1162, (English pp. 953-963).

Simanek et al., "Synthesis of hypecorine and hypecorinine analogs from 3,4-dihydropapaverine," Symp. Pap. IUPAC Int. Symp. Chem. Nat. Prod., 11th (1978), vol. 2, 58-60.

Simanek et al., "Isolation and chemistry of alkaloids from some plants of the family Papaveraceae. Part LXXIV. Synthesis of hypecorine and hypecorinine analogs from 3,4-dihydropapaverine", Heterocycles, 1978, 9(9), pp. 1233-1240.

Sladkov et al., "2,3,10,11-Tetramethoxy-5,6,7,8,13,13a-hexahydroprotoberberines and their B-seco analogs: Synthesis and antineoplastic activity," Khimiko-Farmatsevticheskii Zhurnal (1989), 23(1), 50-3. (Russian language).

Sladkov et al., "Benzophenanthridines. VI. Conversions of protoberberine alkaloids into benzo[c]phenanthridines. Hofmann degradation of α-N- and β-N-methyl-(±)-13α-hydroxyxylopinine iodides," Zhurnal Organicheskoi Khimii (1989), 25(4), 854-62 (Russian language).

Tolkachev et al., "Application of the Willgerodt-Kindler reaction in the synthesis of the 1-benzyl-1,2,3,4-tetrahydroisoquinoline alkaloids and their derivatives," Symp. Pap. IUPAC Int. Symp. Chem. Nat. Prod., 11th (1978), vol. 3, 47-50.

Trifonov et al., "Application of organic photochemistry in the synthesis of (±)-glaucine," Izvestiya po Khimiya (1978), 11(2), 297-304.

Trifonov et al., "Berbin-8-ones from 2'-halo-1-benzylisoquinolines and metal carbonyls," Tetrahedron Letters (1985), 26(26), 3159-62.

Uematsu et al., "Asymmetric transfer hydrogenation of imines," Journal of the American Chemical Society (1996), 118, 4916-4917.

Walterova et al., "Isolation and chemistry of the alkaloids from some plants of the genus Papaver. LXXVII. Pseudobase formation in 2-methylpapaverinium cations and their biotransformation by enzymes of rat liver homogenates in vitro," Collection of Czechoslovak Chemical Communications (1980), 45(3), 956-65.

Wert et al., "Hofmann degradation of β-hydroxy ammonium salts. α- and β-hydroxylaudanosine, 7-hydroxyglaucine, and 13-hydroxyxylopinine," Journal of Organic Chemistry (1982), 47(26), 5141-50.

Williams et al., "One-pot formation of nitrogen-containing heterocyclic ring systems using a deprotection-cyclization-asymmetric reduction sequence," Chemical Communications Cambridge, United Kingdom) (2005), (37), 4735-4737.

Yamada et al., "Studies on 1,2,3,4-tetrahydroisoquinolines. VI. Reutilization of the unwanted (R)-isomer of (S)-(−)-5,7-dihydroxy-1-(3,4,5-trimethoxybenzyl)-1,2,3,4-tetrahydroisoquinoline (TA-073)," Chemical and Pharmaceutical Bulletin (1983), 31(1), 70-4.

Zhao et al., "Synthesis of nitrones from 3,4-dihydroisoquinoline derivatives by oxidation with m-chloroperoxybenzoic acid," Organic Preparations and Procedures International (1997), 29(2), 185-194.

* cited by examiner

PREPARATION OF SUBSTITUTED MORPHINAN-6-ONES AND SALTS AND INTERMEDIATES THEREOF

CROSS REFERENCE TO RELATED APPLICATIONS

This application is a national stage application of PCT/US2007/019489, filed Sep. 6, 2007, which claims the benefit of U.S. Provisional Application No. 60/845,956 filed Sep. 20, 2006 and U.S. Provisional Application No. 60/940,463 filed May 29, 2007.

FIELD OF THE INVENTION

The present invention generally relates to processes for the synthesis of intermediates used to prepare morphinans. More specifically, the invention is directed to the synthesis of substituted morphinan-6-ones and salts, intermediates, and analogs thereof.

BACKGROUND OF THE INVENTION

Morphinan-6-ones are important synthetic intermediates to many opium alkaloid compounds including buprenorphine, codeine, diacetylmorphine, dihydrocodeine, dihydroetorphine, diprenorphine, etorphine, hydrocodone, hydromorphone, morphine, nalbuphene, nalmefene, naloxone, naltrexone, oxycodone, and oxymorphone. Generally, these compounds are analgesics, which are used extensively for pain relief in the field of medicine due to their action as opiate receptor agonists. However, nalmefene, naloxone, and naltrexone are opiate receptor antagonists; and are used for reversal of narcotic/respiratory depression due to opiate receptor agonists.

Various processes for the total synthesis of morphinan-6-ones such as through the intermediate nordihydrothebaineone are known. In U.S. Pat. Nos. 4,368,326 and 4,521,601, for example, Rice discloses the N-formylation of a tetrahydroisoquinoline using ethyl formate or phenyl formate, respectively. Rice further discloses reacting the tetrahydroisoquinoline with ethylene glycol, and brominating the resulting ketal. After removing the ketal protecting group to form a bromoketone, Rice prepares a nordihydrothebaineone (e.g., 1-(2'-bromo-4'-methoxy-5'-hydroxybenzyl)-2-formyl-1,3,4,5,7,8-hexahydroisoquinolin-6-one) from the bromoketone by Grewe cyclization catalyzed using a super acid medium alone or with a combination of an ammonium fluoride complex and hydrogen fluoride or trifluoromethanesulfonic acid.

The presence of water and other contaminants in the reaction mixtures of various synthetic steps employed in the formation of morphinan-6-ones and analogs and intermediates thereof is one factor that affects the reproducibility and yields of such steps. Contaminants in the starting β,γ-hexahydroisoquinoline reaction mixture used in the Grewe cyclization, for example, cause reproducibility problems and low yields of the desired cyclized products.

Although the techniques of Rice and others are generally useful for the preparation of various morphinan-6-ones and salts, intermediates, and analogs thereof, there are limitations to their effectiveness and/or efficiency including, for example, the crystallization and re-solubilization of intermediate compounds, material losses in crystallization and transfer, relatively lengthy reaction times, and an increased likelihood of impurities and/or by-product formation. As a result of the higher level of impurities and/or by-products, lower yields of the cyclized morphinan-6-one product are obtained. Accordingly, a need remains for additional processes for the preparation of morphinan-6-ones and salts, intermediates, and analogs thereof having improved reaction times, product yields, and fewer impurities and/or by-products.

SUMMARY OF THE INVENTION

Among the various aspects of the present invention is the provision of a process for the conversion of a hexahydroisoquinoline to a ketal without an intermediate crystallization of an N-formyl derivative. The ketal may then be derivatized by a series of steps to form a morphinan-6-one or salt thereof. For example, the ketal may be converted to a haloketal, the haloketal may be converted to a haloketone, the haloketone may be converted to a morphinan-6-one, and the morphinan-6-one may be converted to a morphinan-6-one salt. In various embodiments, one or more of the synthesis stages are carried out without an intermediate crystallization of an intermediate compound from the reaction product mixture of the previous stage(s).

Briefly, therefore, the present invention is directed to a process for the preparation of a ketal (1000), the process comprising converting a hexahydroisoquinoline (800) to a ketal (1000) in a series of steps, the series of steps comprising (a) converting hexahydroisoquinoline (800) to an N-formyl derivative (900) with a formylating agent and (b) converting the N-formyl derivative (900) to the ketal (1000) with a ketalizing agent in the presence of an acid catalyst, whereby the conversion of the hexahydroisoquinoline (800) to the ketal (1000) proceeds without an intermediate crystallization of the N-formyl derivative (900); wherein the hexahydroisoquinoline (800), the N-formyl derivative (900), and the ketal (1000) correspond to Formulae (800), (900), and (1000), respectively:

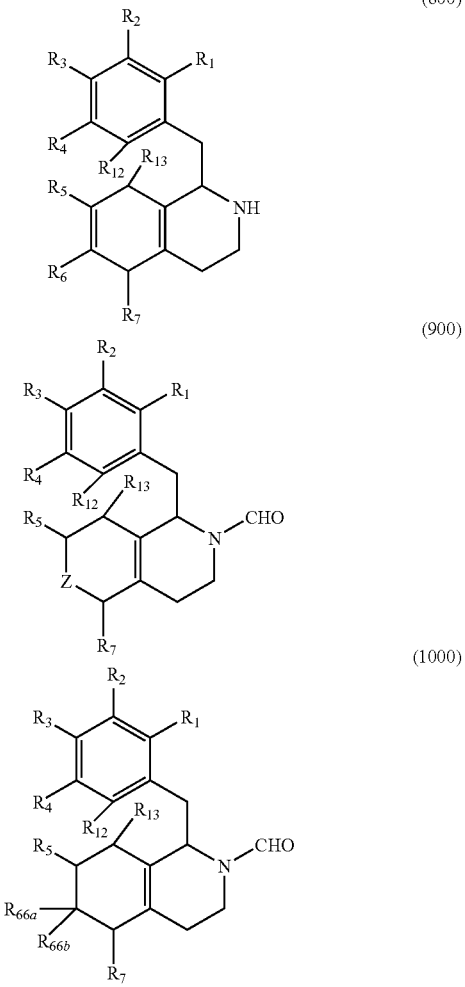

$R_1$ and $R_7$ are independently hydrogen, hydrocarbyl, substituted hydrocarbyl, or $-OR_{111}$;

$R_5$ and $R_6$ are independently hydrogen, hydrocarbyl, substituted hydrocarbyl, or $-OR_{511}$;

$R_2$ is hydrogen, hydrocarbyl, substituted hydrocarbyl, halo, or $-OR_{211}$;

$R_3$ is hydrogen, hydrocarbyl, substituted hydrocarbyl, or $-OR_{311}$;

$R_4$ is hydrogen, hydrocarbyl, substituted hydrocarbyl, halo, or $-OR_{411}$;

$R_{66a}$ and $R_{66b}$ are independently selected from the group consisting of alkoxy and alkylthio or together with the carbon atom to which they are attached form a ketal, dithioketal, or monothioketal;

$R_{12}$ is hydrogen, hydrocarbyl, substituted hydrocarbyl, halo, or $-OR_{121}$;

$R_{13}$ is hydrogen, hydrocarbyl, substituted hydrocarbyl, halo, or $-OR_{511}$;

$R_{111}$ is hydrogen, hydrocarbyl, substituted hydrocarbyl, or a hydroxy protecting group;

$R_{121}$ is hydrogen, hydrocarbyl, or substituted hydrocarbyl;

$R_{211}$ is hydrogen, hydrocarbyl, substituted hydrocarbyl, or a hydroxy protecting group;

$R_{311}$ is hydrogen, hydrocarbyl, substituted hydrocarbyl, or a hydroxy protecting group;

$R_{411}$ is hydrogen, hydrocarbyl, substituted hydrocarbyl, or a hydroxy protecting group;

$R_{511}$ is hydrogen, hydrocarbyl, substituted hydrocarbyl, or a hydroxy protecting group; and —Z— is

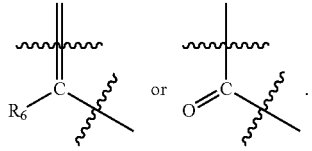

Other objects and features will be in part apparent and in part pointed out hereinafter.

DETAILED DESCRIPTION OF THE INVENTION

The present invention is directed to improved synthetic methods for the preparation of morphinan-6-ones and salts, intermediates, and analogs thereof. Among the various aspects of the present invention is the preparation of various morphinan-6-ones by derivatizing various hexahydroisoquinolines without an intermediate crystallization of one or more intermediate compounds from the reaction product mixtures prior to the next synthetic step in the process. Further, water scavengers may be employed in one or more of the various synthetic steps to provide substantially anhydrous conditions, which can reduce the formation of undesirable by-products and/or other impurities.

One aspect of the present invention is generally directed to the replacement and/or optimization of the liquid composition in which one or more steps of a multistep synthesis of a morphinan-6-one from a hexahydroisoquinoline starting material is carried out. In particular, the liquid composition (e.g., a solvent, a solvent system (i.e., a mixture of solvents), or reactants) in which each intermediate compound is formed in one stage of reaction (e.g., a first solvent) may be removed and predominantly replaced with another liquid composition (e.g., a second solvent) prior to performing the next stage, such that the next stage may be carried out without crystallizing the intermediate compound from the reaction product mixture. This may be accomplished, for example, by employing a second solvent or other composition that has a boiling point that is greater than the boiling point of the first solvent in the reaction product mixture and thereafter heating the product mixture to a temperature in excess of the boiling point of the first solvent. Alternatively, a water soluble solvent may be used as a first or second solvent and may be removed and replaced with a water immiscible solvent by washing with an aqueous solution comprising water and extracting the desired product in the water immiscible solvent.

For purposes of illustration, Reaction Scheme 1 depicts the conversion of a hexahydroisoquinoline starting material (800) to a morphinan-6-one salt (1400) in accordance with one embodiment of the present invention, wherein $R_1, R_2, R_3, R_4, R_5, R_6, R_{66a}, R_{66b}, R_7, R_{12}, R_{13}$, X, Y, and —Z— are as defined below.

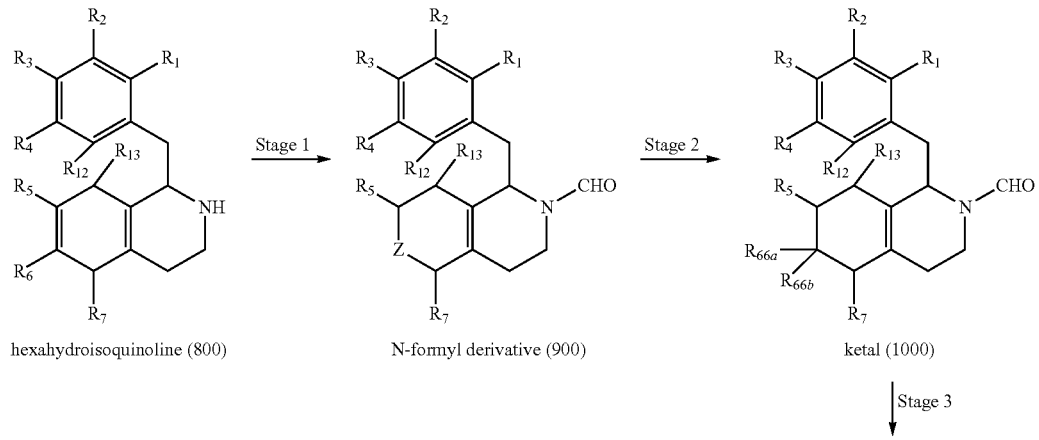

Reaction Scheme 1

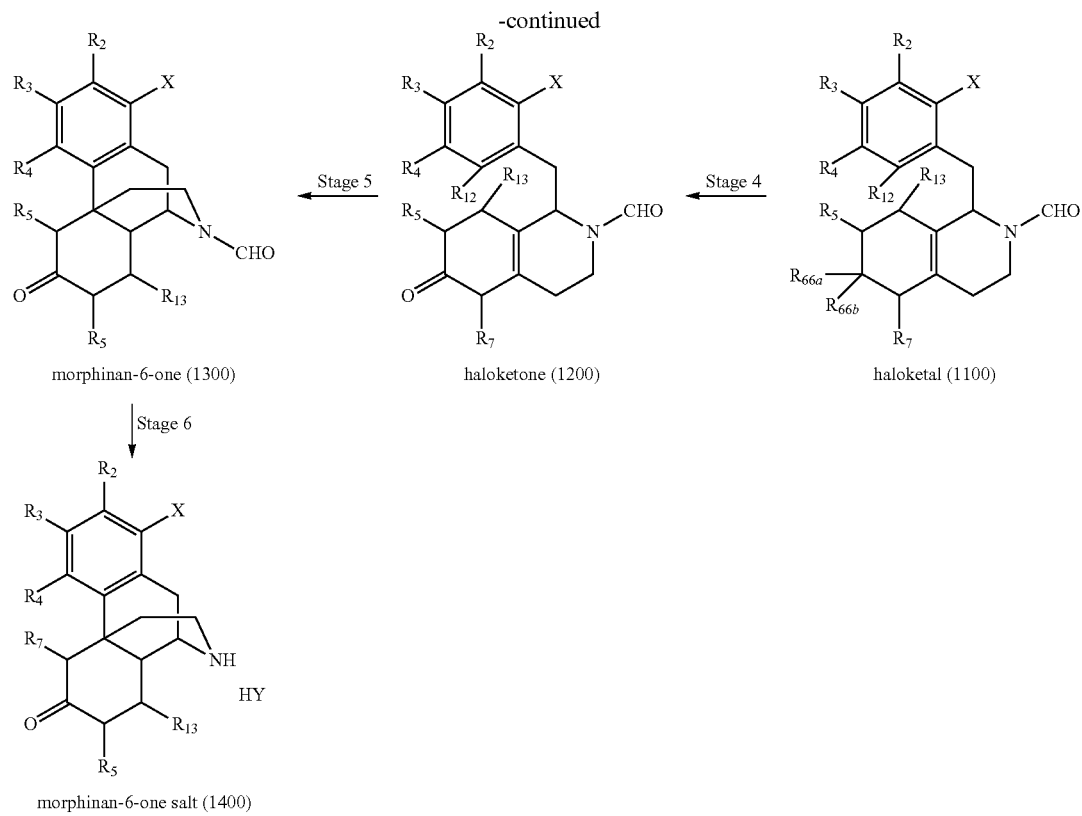

morphinan-6-one (1300) ← Stage 5 ← haloketone (1200) ← Stage 4 ← haloketal (1100)

↓ Stage 6 morphinan-6-one salt (1400)

Advantageously, the solvent replacement and/or optimization techniques described above may be employed in one or more of the various stages depicted in Reaction Scheme 1, thus enabling two or more (or even all) of the stages to be carried out in "one pot." Thus, for example, ketal (1000) can be produced from hexahydroisoquinoline (800) without an intermediate crystallization of N-formyl derivative (900) from a formylation product mixture; haloketal (1100) can be produced from N-formyl derivative (900) without an intermediate crystallization of ketal (1000) from a ketalization product mixture; haloketone (1200) can be produced from ketal (1000) without an intermediate crystallization of haloketal (1100) from a halogenation product mixture; morphinan-6-one (1300) can be produced from haloketal (1100) without an intermediate crystallization of haloketone (1200) from a hydrolyzation product mixture; and morphinan-6-one salt (1400) can be produced from haloketone (1200) without an intermediate crystallization of morphinan-6-one (1300) from a cyclization product mixture.

Additionally, for example, haloketal (1100) can be produced from hexahydroisoquinoline (800) without an intermediate crystallization of N-formyl derivative (900) and/or ketal (1000) from a formylation and/or ketalization product mixture; haloketone (1200) can be produced from N-formyl derivative (900) without an intermediate crystallization of ketal (1000) and/or haloketal (1100) from a ketalization and/or halogenation product mixture; morphinan-6-one (1300) can be produced from ketal (1000) without an intermediate crystallization of haloketal (1100) and/or haloketone (1200) from a halogenation and/or hydrolyzation product mixture; and morphinan-6-one salt (1400) can be produced from haloketal (1100) without an intermediate crystallization of haloketone (1200) and/or morphinan-6-one (1300) from a hydrolyzation and/or cyclization product mixture.

Further, haloketone (1200) can be produced from hexahydroisoquinoline (800) without an intermediate crystallization of N-formyl derivative (900), ketal (1000), and/or haloketal (1100) from a formylation, ketalization, and/or halogenation product mixture; morphinan-6-one (1300) can be produced from N-formyl derivative (900) without an intermediate crystallization of ketal (1000), haloketal (1100), and/or haloketone (1200) from a ketalization, halogenation, and/or hydrolyzation product mixture; and morphinan-6-one salt (1400) can be produced from ketal (1000) without an intermediate crystallization of haloketal (1100), haloketone (1200), and/or morphinan-6-one (1300) from a halogenation, hydrolyzation, and/or cyclization product mixture.

Still further, morphinan-6-one (1300) can be produced from hexahydroisoquinoline (800) without an intermediate crystallization of N-formyl derivative (900), ketal (1000), haloketal (1100), and/or haloketone (1200) from a formylation, ketalization, halogenation, and/or hydrolyzation product mixture; morphinan-6-one salt (1400) can be produced from N-formyl derivative (900) without an intermediate crystallization of ketal (1000), haloketal (1100), haloketone (1200), and/or morphinan-6-one (1300) from a ketalization, halogenation, hydrolyzation, and/or cyclization product mixture, and morphinan-6-one salt (1400) can be produced from hexahydroisoquinoline (800) without an intermediate crystallization of N-formyl derivative (900), ketal (1000), haloketal (1100), haloketone (1200), and/or morphinan-6-one (1300) from a formylation, ketalization, halogenation, hydrolyzation, and/or cyclization product mixture.

As noted above, water scavengers may be used in one or more of the above synthetic stages. Advantageously, the water scavenger can react, remove, and/or irreversibly bind trace amounts of water that may be present in the reaction mixtures of the above synthetic stages, reducing the formation of undesirable side products and/or impurities.

Morphinan-6-one Salts

As described above for Reaction Scheme 1, one aspect of the present invention is a process for the preparation of morphinan-6-one salts corresponding to Formula (1400):

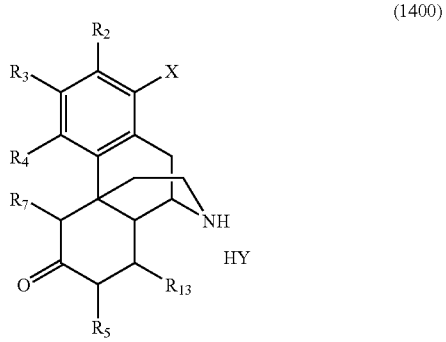

(1400)

wherein $R_2$ is hydrogen, hydrocarbyl, substituted hydrocarbyl, halo, or —$OR_{211}$;

$R_3$ is hydrogen, hydrocarbyl, substituted hydrocarbyl, or —$OR_{311}$;

$R_4$ is hydrogen, hydrocarbyl, substituted hydrocarbyl, halo, or —$OR_{411}$;

$R_5$ is hydrogen, hydrocarbyl, substituted hydrocarbyl, or —$OR_{511}$;

$R_7$ is hydrogen, hydrocarbyl, substituted hydrocarbyl, or —$OR_{511}$;

$R_{13}$ is hydrogen, hydrocarbyl, substituted hydrocarbyl, or —$OR_{511}$;

$R_{211}$ is hydrogen, hydrocarbyl, substituted hydrocarbyl, or a hydroxy protecting group;

$R_{311}$ is hydrogen, hydrocarbyl, substituted hydrocarbyl, or a hydroxy protecting group;

$R_{411}$ is hydrogen, hydrocarbyl, substituted hydrocarbyl, or a hydroxy protecting group;

$R_{511}$ is hydrogen, hydrocarbyl, substituted hydrocarbyl, or a hydroxy protecting group;

X is halo; and

Y is a counterion.

Although $R_2$ may be selected from hydrogen, hydrocarbyl, substituted hydrocarbyl, halo, and —$OR_{211}$, in certain embodiments, $R_2$ is hydrogen or —$OR_{211}$. Where $R_2$ is —$OR_{211}$, for example, $R_{211}$ may be selected from hydrogen, hydrocarbyl, substituted hydrocarbyl, or a hydroxy protecting group. For example, $R_{211}$ may be hydrogen, alkyl, acyl, alkaryl, aryl, or a hydroxy protecting group. In a particular embodiment, $R_{211}$ is hydrogen or alkyl; in this embodiment, $R_{211}$ may be, for example, hydrogen, methyl, ethyl, propyl, butyl, pentyl, or hexyl. In another particular embodiment, $R_{211}$ is hydrogen, acyl, alkaryl, aryl, or a hydroxy protecting group; in this embodiment, $R_{211}$ may be, for example, phenyl, benzyl, tetrahydropyranyl, and the like.

Similarly, although $R_3$ may be selected from hydrogen, hydrocarbyl, substituted hydrocarbyl, and —$OR_{311}$, in certain embodiments, $R_3$ is hydrogen or —$OR_{311}$. Where $R_3$ is —$OR_{311}$, for example, $R_{311}$ may be selected from hydrogen, hydrocarbyl, substituted hydrocarbyl, or a hydroxy protecting group. For example, $R_{311}$ may be hydrogen, alkyl, acyl, alkaryl, aryl, or a hydroxy protecting group. In a particular embodiment, $R_{311}$ is hydrogen or alkyl; in this embodiment, $R_{311}$ may be, for example, hydrogen, methyl, ethyl, propyl, butyl, pentyl, or hexyl. In another particular embodiment, $R_{311}$ is hydrogen, acyl, alkaryl, aryl, or a hydroxy protecting group; in this embodiment, $R_{311}$ may be, for example, phenyl, benzyl, tetrahydropyranyl, and the like.

As noted above, $R_4$ may be selected from hydrogen, hydrocarbyl, substituted hydrocarbyl, halo, and —$OR_{411}$, in certain embodiments, $R_4$ is hydrogen or —$OR_{411}$. Where $R_4$ is —$OR_{411}$, for example, $R_4$ may be selected from hydrogen, hydrocarbyl, substituted hydrocarbyl, or a hydroxy protecting group. For example, $R_{411}$ may be hydrogen, alkyl, acyl, alkaryl, aryl, or a hydroxy protecting group. In a particular embodiment, $R_{411}$ is hydrogen or alkyl; in this embodiment, $R_{411}$ may be, for example, methyl, ethyl, propyl, butyl, pentyl, or hexyl. In another particular embodiment, $R_{411}$ is hydrogen, acyl, alkaryl, aryl, or a hydroxy protecting group; in this embodiment, $R_{411}$ may be, for example, phenyl or benzyl.

In certain embodiments, $R_5$, $R_7$, and $R_{13}$ are preferably hydrogen.

In combination, among certain of the preferred embodiments are morphinan-6-one salts corresponding to Formula (1400) wherein $R_2$ is hydrogen or —$OR_{211}$; $R_3$ is hydrogen or —$OR_{311}$; $R_4$ is hydrogen or —$OR_{411}$; and $R_{211}$, $R_{311}$, and $R_{411}$, are independently selected from hydrogen, hydrocarbyl, substituted hydrocarbyl, or a hydroxy protecting group. In these embodiments, for example, $R_{211}$ is preferably hydrogen, alkyl, acyl, alkaryl, aryl, or a hydroxy protecting group, more preferably hydrogen, methyl, benzyl, or phenyl; $R_{311}$ is preferably hydrogen, alkyl, acyl, alkaryl, aryl, or a hydroxy protecting group, more preferably, hydrogen or alkyl, still more preferably, hydrogen or methyl; $R_{411}$ is preferably hydrogen, alkyl, acyl, alkaryl, aryl, or a hydroxy protecting group, more preferably, hydrogen, alkyl, alkaryl, or aryl, still more preferably hydrogen, methyl, benzyl, or phenyl. In many of these embodiments, $R_5$, $R_7$, and $R_{13}$ are hydrogen.

In a preferred embodiment, X is chloro or bromo; in one particular embodiment, X is bromo.

In a particular embodiment, the morphinan-6-one salt corresponds to Formula (1400), wherein $R_2$, $R_5$, $R_7$, and $R_{13}$ are hydrogen, $R_3$ is —$OR_{311}$, $R_4$ is —OH, $R_{311}$ is alkyl, X is halo, and Y is a counterion. Thus, in this embodiment, the morphinan-6-one salt corresponds to Formula (140):

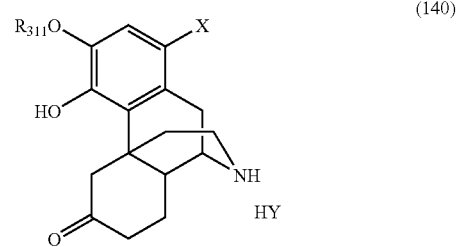

(140)

In another embodiment, the morphinan-6-one salt corresponds to Formula (141):

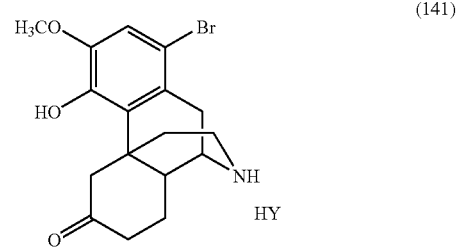

(141)

wherein Y is a counterion. The counterion may be, for example, fumarate, tartrate, bitartrate, oxalate, sulfate, bisulfate, phosphate, dihydrogen phosphate, tetrafluoroborate, hexafluorophosphate, methanesulfonate, acetate, trifluoroacetate, trifluoromethanesulfonate, chloride, bromide, iodide, and the like. In a particular embodiment, the counterion is bromide.

Morphinan-6-ones

As described above for Reaction Scheme 1, another aspect of the present invention is a process for the preparation of a morphinan-6-one corresponding to Formula (1300):

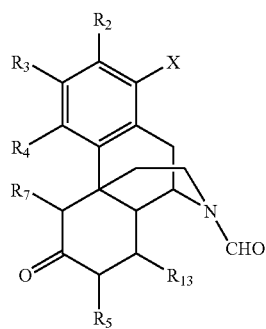
(1300)

wherein $R_2$, $R_3$, $R_4$, $R_5$, $R_7$, $R_{13}$, and X are as defined in connection with Formula (1400) above.

In a particular embodiment, the morphinan-6-one corresponds to Formula (1300) wherein $R_2$, $R_5$, $R_7$, and $R_{13}$ are hydrogen, $R_3$ is —$OR_{311}$, $R_4$ is —OH, $R_{311}$ is alkyl, and X is halo. Thus, in this embodiment, the morphinan-6-one corresponds to Formula (130):

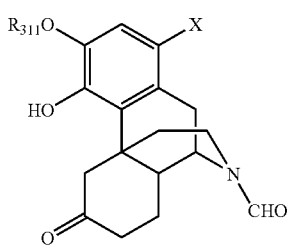
(130)

In another embodiment, the morphinan-6-one corresponds to Formula (13):

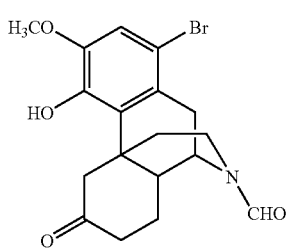
(13)

Haloketones

As described above for Reaction Scheme 1, another aspect of the present invention is a process for the preparation of a haloketone corresponding to Formula (1200):

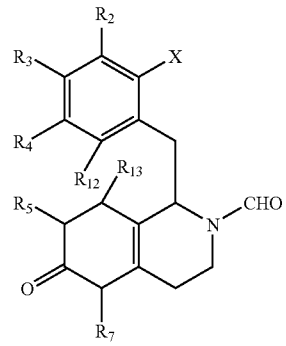
(1200)

wherein
$R_{12}$ is hydrogen, hydrocarbyl, substituted hydrocarbyl, halo, or —$OR_{121}$;
$R_{121}$ is hydrogen, hydrocarbyl, or substituted hydrocarbyl; and
$R_2$, $R_3$, $R_4$, $R_5$, $R_7$, $R_{13}$, and X are as defined in connection with Formulae (1300) and/or (1400) above.

Although $R_{12}$ may be selected from hydrogen, hydrocarbyl, substituted hydrocarbyl, halo, and —$OR_{121}$, in some embodiments, $R_{12}$ is hydrogen, alkyl, alkenyl, aryl, aralkyl, or halo. Where $R_{12}$ is —$OR_{121}$, for example, $R_{121}$ is selected from hydrogen, hydrocarbyl, or substituted hydrocarbyl. In a particular embodiment, $R_{12}$ is hydrogen, alkyl, allyl, benzyl, or halo. In certain embodiments, $R_{12}$ and $R_{13}$ are preferably hydrogen.

In a particular embodiment, the haloketone corresponds to Formula (1200) wherein $R_2$, $R_5$, $R_7$, $R_{12}$, and $R_{13}$ are hydrogen, $R_3$ is —$OR_{311}$, $R_4$ is —OH, $R_{311}$ is alkyl, and X is halo. Thus, in this embodiment, the haloketone corresponds to Formula (120):

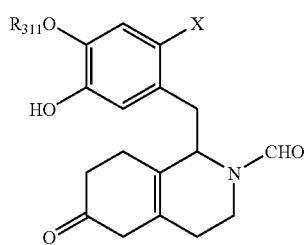
(120)

In another embodiment, the haloketone corresponds to Formula (12):

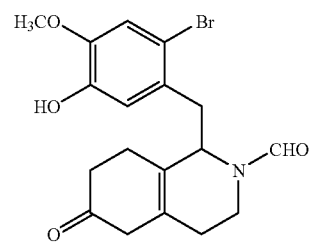
(12)

Haloketals

As described above for Reaction Scheme 1, another aspect of the present invention is a process for the preparation of a haloketal corresponding to Formula (1100):

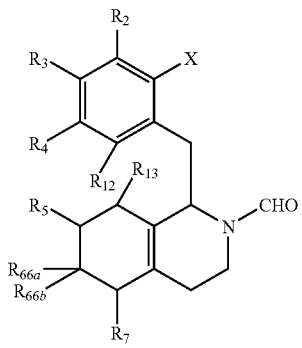

(1100)

wherein $R_{66a}$ and $R_{66b}$ are independently selected from the group consisting of alkoxy and alkylthio or together with the carbon atom to which they are attached form a ketal, dithioketal, or monothioketal; and $R_2$, $R_3$, $R_4$, $R_5$, $R_7$, $R_{12}$, $R_{13}$, and X are as defined in connection with Formulae (1200), (1300), and/or (1400) above.

Although $R_{66a}$ and $R_{66b}$ may be independently selected from the group consisting of alkoxy and alkylthio or together with the carbon atom to which they are attached form a ketal, dithioketal, or monoketal, in certain embodiments, $R_{66a}$ and $R_{66b}$ together with the carbon atom to which they are attached form a ketal.

In a particular embodiment, the haloketal corresponds to Formula (1100) wherein $R_2$, $R_5$, $R_7$, $R_{12}$, and $R_{13}$ are hydrogen, $R_3$ is —$OR_{311}$, $R_4$ is —OH, $R_{66a}$ and $R_{66b}$ together with the carbon atom to which they are attached form a ketal, and $R_{311}$ is alkyl. Thus, in this embodiment, the haloketal corresponds to Formula (110):

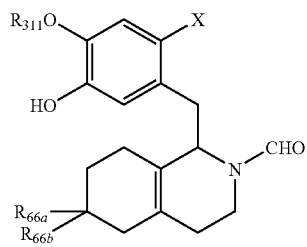

(110)

In another embodiment, the haloketal corresponds to Formula (11):

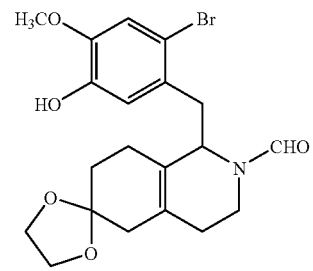

(11)

Ketals

As described above for Reaction Scheme 1, another aspect of the present invention is a process for the preparation of a ketal corresponding to Formula (1000):

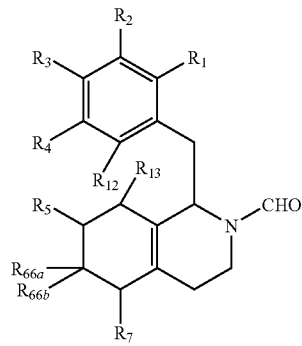

(1000)

wherein $R_1$ is hydrogen, hydrocarbyl, substituted hydrocarbyl, or —$OR_{111}$;

$R_{111}$ is hydrogen, hydrocarbyl, substituted hydrocarbyl, or a hydroxy protecting group; and $R_2$, $R_3$, $R_4$, $R_5$, $R_{66a}$, $R_{66b}$, $R_7$, $R_{12}$, and $R_{13}$ are as defined in connection with Formulae (1100), (1200), (1300), and/or (1400) above.

Although $R_1$ may be selected from hydrogen, hydrocarbyl, substituted hydrocarbyl, and —$OR_{111}$, in certain embodiments, $R_1$ is hydrogen or —$OR_{111}$. Where $R_1$ is —$OR_{111}$, for example, $R_{111}$ may be selected from hydrogen, hydrocarbyl, substituted hydrocarbyl, or a hydroxy protecting group. For example, $R_{111}$ may be hydrogen, alkyl, acyl, alkaryl, aryl, or a hydroxy protecting group. In a particular embodiment, $R_{111}$ is hydrogen or alkyl; in this embodiment, $R_{111}$ may be, for example, hydrogen, methyl, ethyl, propyl, butyl, pentyl, or hexyl. In another particular embodiment, $R_{111}$ is hydrogen, acyl, alkaryl, aryl, or a hydroxy protecting group; in this embodiment, $R_{111}$ may be, for example, phenyl or benzyl.

In a particular embodiment, the ketal corresponds to Formula (1000) wherein $R_1$, $R_2$, $R_5$, $R_7$, $R_{12}$, and $R_{13}$ are hydrogen, $R_3$ is —$OR_{311}$, $R_4$ is —OH, $R_{66a}$ and $R_{66b}$ together with the carbon atom to which they are attached form a ketal, and $R_{311}$ is alkyl. Thus, in this embodiment the ketal corresponds to Formula (100):

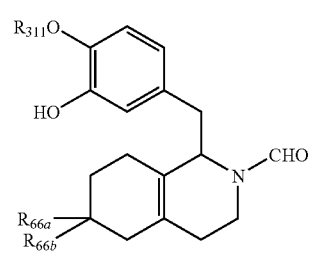

(100)

In another embodiment, the ketal corresponds to Formula (10):

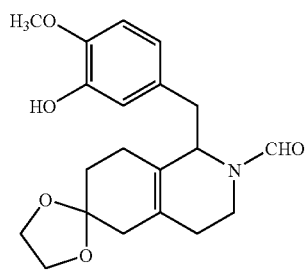
(10)

N-Formyl Derivatives

As described above for Reaction Scheme 1, another aspect of the present invention is a process for the preparation of an N-formyl derivative corresponding to Formula (900):

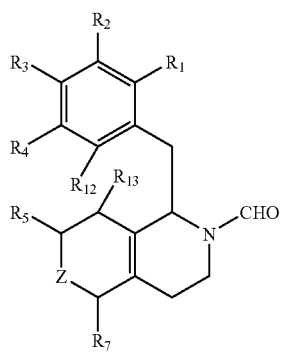
(900)

wherein $R_6$ is hydrogen, hydrocarbyl, substituted hydrocarbyl, or —$OR_{511}$;

$R_{511}$ is hydrogen, hydrocarbyl, substituted hydrocarbyl, or a hydroxyl protecting group;

—Z— is

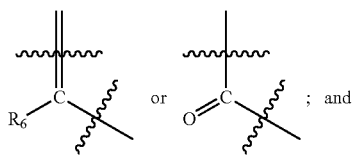

$R_1$, $R_2$, $R_3$, $R_4$, $R_5$, $R_7$, $R_{12}$, and $R_{13}$ are as defined in connection with Formulae (1000), (1100), (1200), (1300), and/or (1400) above.

As noted above, —Z— is

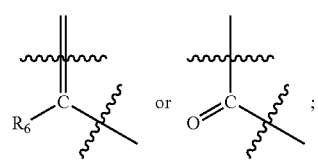

thus, the N-formyl derivative (900) may correspond to either Formulae (901) or (902):

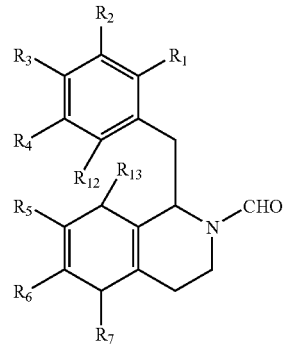
(901)

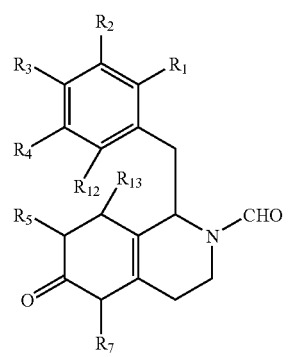
(902)

wherein $R_1$, $R_2$, $R_3$, $R_4$, $R_5$, $R_6$, $R_7$, $R_{12}$, and $R_{13}$ are as defined in connection with Formulae (1000), (1100), (1200), (1300), and/or (1400) above.

In the embodiments in which —Z— is

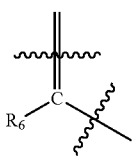

(i.e., where the N-formyl derivative corresponds to Formula (901)), $R_6$ may be selected from hydrogen, hydrocarbyl, substituted hydrocarbyl, and —$OR_{511}$. In some embodiments, $R_6$ is hydrogen or —$OR_{511}$. Where $R_6$ is —$OR_{511}$, for example, $R_{511}$ may be selected from hydrogen, hydrocarbyl, substituted hydrocarbyl, or a hydroxy protecting group. For example, $R_{511}$ may be hydrogen, alkyl, acyl, alkaryl, aryl, or a hydroxy protecting group. In a particular embodiment, $R_{511}$ is hydrogen, methyl, ethyl, propyl, butyl, pentyl, or hexyl; more preferably in this embodiment, $R_{511}$ is methyl. In another particular embodiment, $R_{511}$ is hydrogen, acyl, alkaryl, aryl, or a hydroxy protecting group; in this embodiment, $R_{511}$ may be, for example, phenyl or benzyl.

In a particular embodiment, the N-formyl derivative corresponds to Formula (900) wherein $R_1$, $R_2$, $R_5$, $R_7$, $R_{12}$, and $R_{13}$ are hydrogen, $R_3$ is —$OR_{311}$, $R_4$ is —OH, $R_6$ (if present)

is —$OR_{511}$, $R_{311}$ and $R_{511}$ (if present) are independently alkyl, and —Z— is

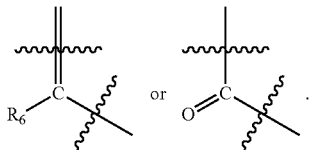

Thus, in this embodiment, the N-formyl derivative corresponds to Formula (91) or Formula (92):

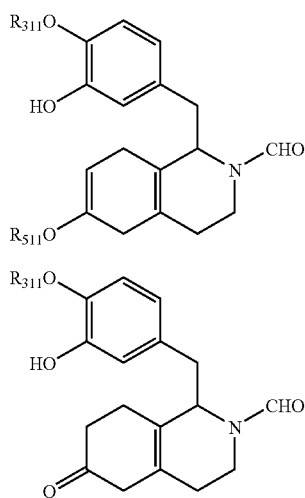

In another embodiment, the N-formyl derivative corresponds to Formula (9A):

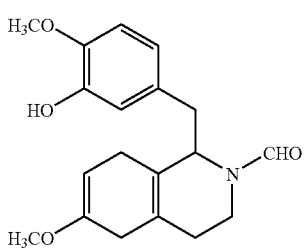

In another embodiment, the N-formyl derivative corresponds to Formula (9B):

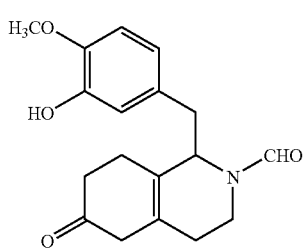

Hexahydroisoquinolines

As described above for Reaction Scheme 1, a hexahydroisoquinoline corresponding to Formula (800) has the structure:

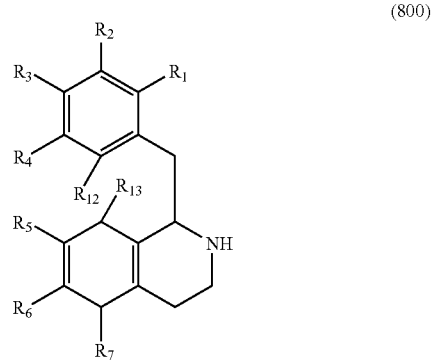

wherein $R_1$, $R_2$, $R_3$, $R_4$, $R_5$, $R_6$, $R_7$, $R_{12}$, and $R_{13}$ are as defined in connection with Formulae (900), (1000), (1100), (1200), (1300), and/or (1400) above.

In a particular embodiment, the hexahydroisoquinoline corresponds to Formula (800) wherein $R_1$, $R_2$, $R_5$, $R_7$, $R_{12}$, and $R_{13}$ are hydrogen, $R_3$ is —$OR_{311}$, $R_4$ is —OH, $R_6$ is —$OR_{511}$, and $R_{311}$ and $R_{511}$ are independently alkyl. Thus, in this embodiment, the hexahydroisoquinoline corresponds to Formula (80):

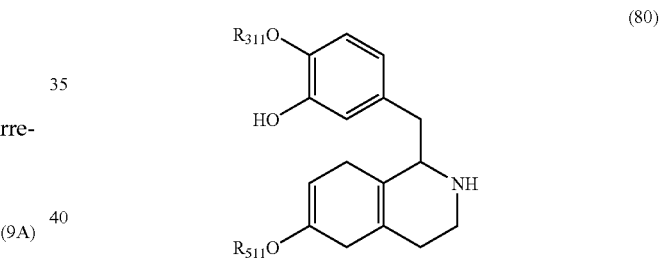

In another embodiment, the hexahydroisoquinoline corresponds to Formula (8):

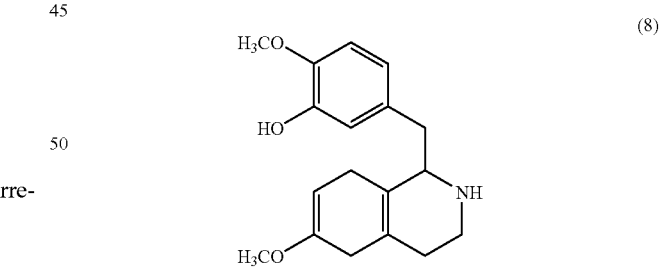

Synthetic Stages

For the processes of the present invention described in Reaction Scheme 1 and in the following synthesis stages, the products, intermediates, and/or starting compounds (e.g., hexahydroisoquinolines, N-formyl derivatives, ketals, haloketals, haloketones, and morphinan-6-ones and salts thereof) are the same as those described in Reaction Scheme 1 above and illustrated in the above-described compounds corresponding to Formulae (800), (900), (1000), (1100), (1200), (1300), and/or (1400). The individual stages described below may be performed alone or in combination with any other synthesis stage to form a desired compound.

N-Formylation of a Hexahydroisoquinoline (800)

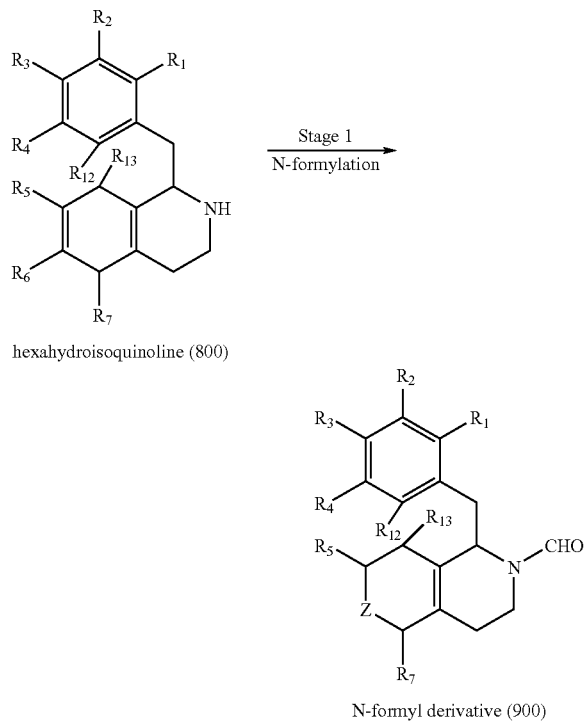

Reaction Scheme 2 hexahydroisoquinoline (800)

N-formyl derivative (900)

As illustrated in Reaction Scheme 2, Stage 1 involves the reaction of a hexahydroisoquinoline (800) with a formylating agent to form an N-formyl derivative (900), wherein $R_1$, $R_2$, $R_3$, $R_4$, $R_5$, $R_6$, $R_7$, $R_{12}$, $R_{13}$, and —Z— are as defined in connection with Formulae (800) and/or (900) above. The formylation reaction mixture typically contains the hexahydroisoquinoline (800) and the formylating agent, and the N-formyl derivative (900) is the reaction product of the hexahydroisoquinoline (800) and the formylating agent.

As described in further detail below, according to certain N-formylation reaction conditions other substituents and bonds may react with the formylating agent in addition to the reaction of the formylating agent and the secondary amino moiety of the hexahydroisoquinoline (800). For instance, in some N-formylation reactions the $R_6$ substituent and the double bond between the carbon atoms carrying the $R_5$ and $R_6$ substituents react with the formylating agent during the N-formylation process; that is, the $R_6$ substituent attached to the C(6) carbon atom and the double bond between the carbon atoms carrying the $R_5$ and the $R_6$ substituents are converted to a keto moiety and a single bond, respectively, during the formylation reaction, shown on the N-formyl derivative (900) as the —Z— moiety, wherein —Z— is

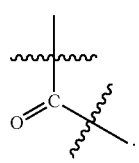

In other N-formylation reactions, only the secondary amino moiety of the hexahydroisoquinoline (800) is formylated and no other substituents or bonds are affected; that is, the $R_6$ substituent and the double bond between the carbon atoms carrying the $R_5$ and $R_6$ substituents are the same as those found on hexahydroisoquinoline (800) (i.e., these substituents are unchanged), shown on the N-formyl derivative (900) as the —Z— moiety, wherein —Z— is

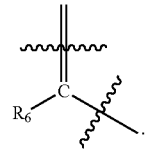

The hexahydroisoquinoline (800) may be in the free base or salt form. In either case, the hexahydroisoquinoline (800) may be optionally combined with an organic solvent to assist in the formation of a substantially homogeneous reaction mixture (e.g., to solubilize the hexahydroisoquinoline (800)). Typically, the hexahydroisoquinoline (800) is combined with the organic solvent in the reaction vessel prior to the addition of the formylating agent. Alternatively, however, the organic solvent and the formylating agent may be combined and thereafter added to the reaction vessel containing the hexahydroisoquinoline (800). Exemplary organic solvents that may be used to solubilize the hexahydroisoquinoline (800) prior to or during reaction with the formylating agent include, but are not limited to, chloroform, dichloromethane, toluene, chlorobenzene, xylene, ethyl acetate, propyl acetate, combinations thereof, and the like. In a particular embodiment, the organic solvent is chloroform or propyl acetate.

A variety of formylating agents may be used in formylating the amino moiety of the hexahydroisoquinoline (800), and suitable formylating agents are known in the art (see, e.g., "Protective Groups in Organic Synthesis" by T. W. Greene and P. G. M. Wuts, John Wiley & Sons, 1999). Thus, for example, the formylating agent may include formic acid or formic acid esters (such as methyl formate, ethyl formate, propyl formate, butyl formate, phenyl formate, benzyl formate, and the like), ammonium formates, trialkylammonium formates (such as triethylammonium formate or triisopropylammonium formate), trialkylorthoformates (such as trimethylorthoformate or triethylorthoformate), or vinyl formates. In a particular embodiment, the formylating agent is a formic acid ester; more preferably in this embodiment, the formylating agent is propyl formate or butyl formate. In another embodiment, the formylating agent includes formic acid.

Where the formylating agent includes formic acid, for example, the N-formylation reaction is typically carried out in the presence of an activating agent. A variety of conventional activating agents may be employed in this stage for the activation of formic acid. For instance, suitable activating agents include, but are not limited to, acetic anhydride, carbodiimides (such as, for example, 1,3-dicyclohexylcarbodiimide (DCC), diisopropylcarbodiimide (DIC), and the like), non-nucleophilic bases (such as, for example, triethylamine, tripropylamine, N,N-diisopropylethylamine, N-methylmorpholine, N-ethylmorpholine, and the like), or mixed anhydrides including an alkyl haloformate or alkanoyl halide (such as, for example, methyl chloroformate, ethyl chloroformate, propyl chloroformate, butyl chloroformate, isobutyl chloroformate, pivaloyl chloride, adamantine carboxyl chloride, and the like) in the presence of a non-nucleophilic base.

In a particular embodiment, the activating agent includes acetic anhydride or a carbodiimide (e.g., DCC, DIC, etc.).

As shown in Reaction Scheme 2 above, the N-formylation reaction protects the secondary amino moiety of the hexahydroisoquinoline (800) with a formyl group. As noted above, depending on the particular formylating agent(s) and methods employed, the N-formylation may or may not result in the reaction and conversion of other substituents and bonds of the hexahydroisoquinoline (800) (e.g., the $R_6$ substituent and the double bond between the carbon atoms carrying the $R_5$ and the $R_6$ substituents).

Where the formylating agent includes a formic acid ester (e.g., methyl formate, ethyl formate, propyl formate, butyl formate, phenyl formate, benzyl formate, and the like), for example, the reaction of the hexahydroisoquinoline (800) with the formic acid ester converts the secondary amino moiety of the hexahydroisoquinoline (800) to an N-formyl moiety. The secondary amino moiety is typically the only moiety on the hexahydroisoquinoline (800) that is affected during the reaction with a formylating agent including a formic acid ester. This N-formylation strategy is generally illustrated in Reaction Scheme 2A, wherein $R_1$, $R_2$, $R_3$, $R_4$, $R_5$, $R_6$, $R_7$, $R_{12}$, and $R_{13}$ are as defined in connection with Formulae (800) and/or (900) above:

Reaction Scheme 2A

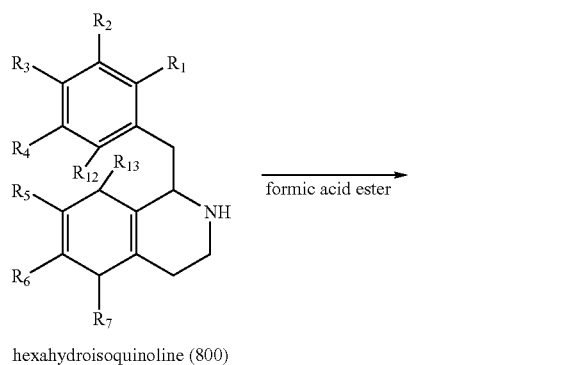

hexahydroisoquinoline (800)

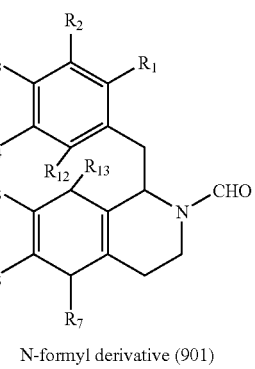

N-formyl derivative (901)

Where the formylating agent includes formic acid, the formic acid is typically activated by the activating agent to form an activated formyl transfer species. Upon reaction of the hexahydroisoquinoline (800) with the formyl transfer species, the secondary amino moiety is formylated. In addition to N-formylation, the formyl transfer species can convert the double bond between the carbon atoms carrying the $R_5$ and the $R_6$ substituents to a single bond and the $R_6$ substituent to a keto moiety. This may occur, for example, by the hydrolysis of the $R_{511}$ substitutent, where $R_6$ is —$OR_{511}$ and $R_{511}$ is hydrocarbyl. Other positions may also be formylated by the formyl transfer agent. For instance, where $R_4$ is hydroxy, this hydroxy group can be protected as the formate ester. Undesired formylated moieties, if present, can be removed by mild basic hydrolysis (e.g., using NaOH) to yield the 6-keto, N-formyl derivative corresponding to Formula (902), which may then be ketalized as described below in Stage 2. This N-formylation strategy is generally illustrated in Reaction Scheme 2B, wherein $R_1$, $R_2$, $R_3$, $R_4$, $R_5$, $R_6$, $R_7$, $R_{12}$, and $R_{13}$ are as defined in connection with Formulae (800) and/or (900) above.

Reaction Scheme 2B

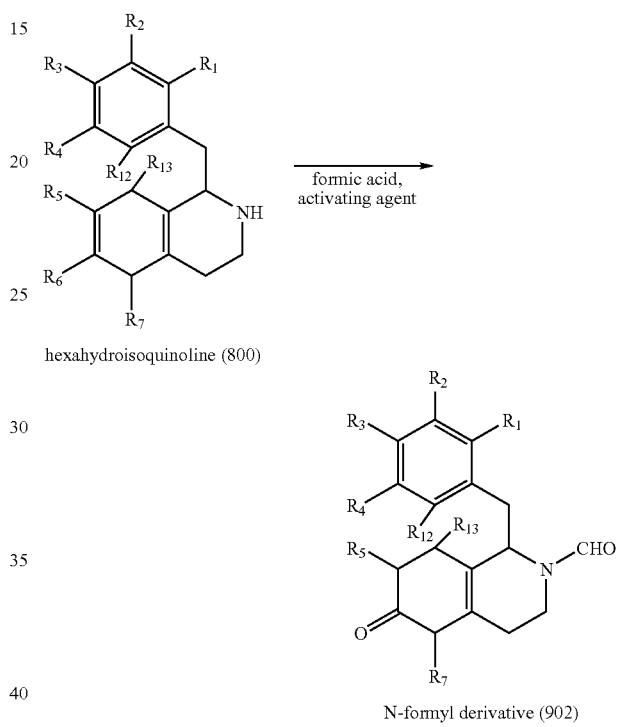

In various embodiments, the formylating agent has a boiling point of at least about 70° C. at 1 atm; thus, for example, the formylating agent may have a boiling point of from about 70° C. to about 90° C., or greater. In a particular embodiment, the formylating agent has a boiling point of at least about 80° C. at 1 atm; preferably in this embodiment, the formylating agent includes propyl formate (boiling point ~82° C. at 1 atm). The atmospheric pressure of the reaction mixture may also be reduced to cause a corresponding reduction in the boiling point of a formylating agent that otherwise has a higher boiling point at ambient pressure. Stated another way, reducing the atmospheric pressure surrounding the reaction mixture can cause butyl formate (boiling point ~107° C. at 1 atm) and/or benzyl formate (boiling point ~203° C. at 1 atm), for example, to boil at temperatures within the above ranges (e.g., less than 100° C., or less than 90° C.).

The use of higher boiling point formylating agents, in general, allows the reaction temperature in Stage 1 of Reaction Scheme 1 to be increased. Advantageously, the increased reaction temperature propels the N-formylation reaction towards completion relatively quickly and efficiently. Using the higher boiling formic acid esters propyl formate or butyl formate, for example, the reaction is typically substantially complete in a matter of 2-8 hours. See, e.g., Example 1.

The formylating agent is typically used in excess such that it can act as both the solvent and the reactant in the reaction mixture (i.e., the secondary amine moiety of the hexahydroisoquinoline (800) is directly condensated with the formylating agent without the use of additional solvent(s) in the reaction mixture). Additionally or alternatively, however, the formylation reaction may take place in the presence of a solvent or solvent system (i.e., a mixture of solvents), such as the solubilizing organic solvent described above, and/or another solvent or solvent system may be added to the reaction mixture after the reaction mixture is complete or substantially complete as determined by thin-layer chromatography, HPLC, or other method. Regardless of whether one or more solvents are present in the reaction mixture, the reaction mixture typically contains from about 3 equivalents to about 50 equivalents of the formylating agent for each equivalent of the hexahydroisoquinoline (800); preferably from about 5 equivalents to about 10 equivalents.

The formylation reaction mixture containing the hexahydroisoquinoline (800) and the formylating agent is generally heated at least until a homogeneous mixture is formed. Preferably, the reaction mixture is heated to reflux. Depending on the particular formylating agent and/or solvent or solvent system utilized, and their corresponding boiling points, the reaction temperatures may vary. Excessive heating, however, tends to cause the alkene of the enol ether to undesirably migrate and/or other positions to react (e.g., formyl protection of other substituents). Typically, the reaction temperature is from about 60° C. to about 100° C.; or from about 70° C. to about 90° C. Similarly, reaction times may vary depending on the various reaction conditions employed (e.g., the particular formylating agent and/or solvent(s) selected, reaction temperature, and the like). Typically, reaction times can range from one hour to five hours, or longer; preferably about five hours. The reaction is typically carried out under ambient pressure; as noted above, however, the pressure may be reduced in order to reduce the boiling point of the formylating agent and/or the solvent(s) utilized in the formylation reaction. The reaction mixture is also typically agitated using conventional means (e.g., manual stirring or by way of a magnetic stirring apparatus). Preferably, the reaction is carded out in an inert atmosphere (e.g., nitrogen or argon); more preferably, the reaction is carried out in a nitrogen atmosphere.

In general, completion of the N-formylation reaction may be monitored according to conventional means (e.g., TLC, HPLC). The resulting formylation product mixture typically contains the N-formyl derivative (900), and unreacted formylating agent. Depending on the temperature at which the formylation is performed, the solvent employed to solubilize the hexahydroisoquinoline (800) before or during formylation may or may not be present (i.e., the reaction mixture may be heated to a temperature in excess of the solvent and the solvent may be distilled off during the formylation reaction).

After the reaction is substantially complete, the excess or unreacted formylating agent may be removed from the formylation product mixture. Alternatively, the formylating agent may be removed from one of the subsequent product mixtures described below, such as the ketalization, halogenation, or hydrolyzation product mixtures. Removal of the unreacted formylating agent is typically accomplished using a liquid composition having a boiling point that is greater than the boiling point of the formylating agent. For example, the liquid composition may have a boiling point of at least about 75° C., at least about 85° C., at least about 95° C., at least about 105° C., at least about 115° C., or greater. In a particular embodiment, the liquid composition has a boiling point of from about 75° C. at 1 atm to about 200° C. at 1 atm; for example, from about 90° C. at 1 atm to about 145° C. at 1 atm. In addition to enabling the removal of the formylating agent, it has been found that the use of such a liquid composition, alone or in combination with the use of a formylating agent having a boiling point of at least 70° C. at 1 atm, enables the reaction temperature in Stage 1 to be increased. As a result, the Stage 1 reaction time is dramatically reduced and yield is improved.

In one embodiment, the liquid composition is a solvent having a boiling point that is greater than the boiling point of the formylating agent. Suitable solvents that may be used in the removal of the formylating agent include, for example, chlorobenzene (boiling point ~131° C. at 1 atm), toluene (boiling point ~110.6° C. at 1 atm), butyl acetate (boiling point ~126° C. at 1 atm), dimethoxyethane (boiling point ~84.5° C. at 1 atm), acetonitrile (boiling point ~81.6° C. at 1 atm), 1,2-dichloroethane (boiling point ~83.5° C. at 1 atm), 1,4-dioxane (boiling point ~101.3° C. at 1 atm), ethyl acetate (boiling point ~77.1° C. at 1 atm), propyl acetate (boiling point ~101.6° C. at 1 atm), ethanol (boiling point ~78.3° C. at 1 atm), 1-butanol (boiling point ~117.7° C. at 1 atm), 2-butanol (boiling point ~99.5° C. at 1 atm), 1-propanol (boiling point ~97.2° C. at 1 atm), 2-propanol (boiling point ~82.2° C. at 1 atm), tert-butanol (boiling point ~82.3° C. at 1 atm), acetic acid (boiling point ~117.9° C. at 1 atm), 2-methoxyethanol (boiling point ~124.6° C. at 1 atm), combinations thereof, and the like. In a particular embodiment, the solvent is propyl acetate.

In another embodiment, the liquid composition is the ketalizing agent utilized in the next synthetic stage of the reaction (i.e., the ketalization reaction of Stage 2 below). According to this embodiment, any of the ketalizing agents described below may be used, provided that the ketalizing agent selected has a boiling point that is greater than the boiling point of the formylating agent. For example, 1,2-ethanediol (boiling point ~197.5° C.) could function as both the ketalizing agent and the liquid composition for formylating agent removal.

In various embodiments, the higher boiling liquid composition may be added to the formylation product mixture after reacting hexahydroisoquinoline (800) with the formylating agent to form the formylation product mixture comprising N-formyl derivative (900) in a solvent system; alternatively, the hexahydroisoquinoline (800) may be reacted with the formylating agent in a liquid composition having a higher boiling point than the boiling point of the formylating agent.

The formylating agent is removed from the formylation product mixture by heating the same to a temperature in excess of the boiling point of the formylating agent. This heating step may also remove any other components present in the formylation product mixture having relatively low boiling points such as, for instance, the organic solvent used to solubilize the hexahydroisoquinoline (800). In essence, the heating step distills off all or substantially all of the lower boiling components from the formylation product mixture, leaving the N-formyl derivative (900) dissolved in the liquid composition having a boiling point that is greater than the boiling point of the formylating agent.

By way of example, the formylation product mixture may contain propyl formate (as the formylating agent; boiling point ~82° C. at 1 atm), chloroform (as the solubilizing organic solvent; boiling point ~61° C. at 1 atm), and propyl acetate (as the solvent having a boiling point greater than the boiling point of the formylating agent; boiling point ~102° C. at 1 atm). Heating the formylation product mixture to a temperature that is in excess of about 82° C. (the boiling point of propyl formate), but below about 102° C. (the boiling point of propyl acetate), will substantially drive off both the chloroform and the propyl formate, leaving the propyl acetate as the predominant solvent in the formylation product mixture.

Preferably, at least 50% (by volume) of the formylating agent is removed from the formylation product mixture. For example, about 55% (by volume), about 60% (by volume), about 65% (by volume), about 70% (by volume), about 75% (by volume), about 80% (by volume), about 85% (by volume), about 95% (by volume), or about 99% (by volume) of the formylating agent may be removed from the formylation product mixture.

Following removal of the formylating agent from the formylation product mixture, the formylation product mixture containing the N-formyl derivative (900) and the liquid composition having a boiling point that is greater than the formylating agent is preferably utilized in Stage 2 of Reaction Scheme 1 (i.e., the ketalization reaction described in further detail below) without an intermediate crystallization of the N-formyl derivative (900). Alternatively, the N-formyl derivative (900) may be crystallized from the formylation product mixture according to conventional methods.

Ketalization of an N-Formyl Derivative (900) to Form a Ketal (1000)

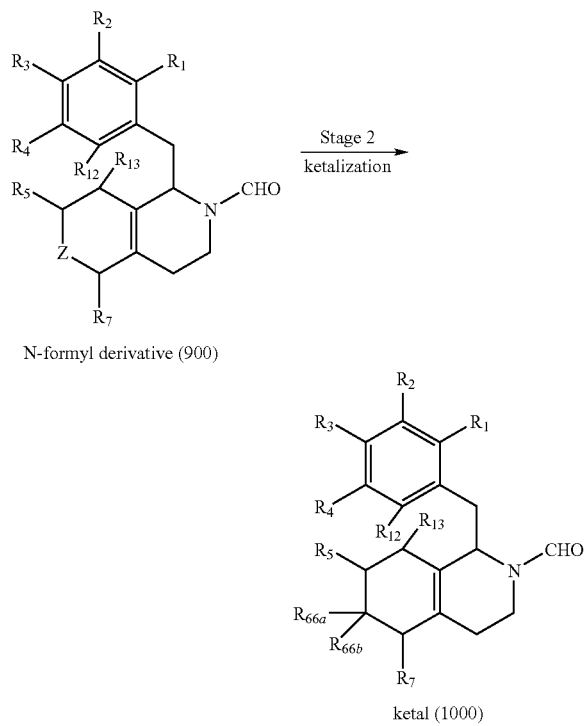

As illustrated in Reaction Scheme 3, Stage 2 involves the reaction of an N-formyl derivative (900) with a ketalizing agent to form a ketal (1000), wherein $R_1$, $R_2$, $R_3$, $R_4$, $R_5$, $R_6$, $R_{66a}$, $R_{66b}$, $R_7$, $R_{12}$, $R_{13}$, and —Z— are as defined in connection with Formulae (800), (900), and/or (1000) above. The ketal (1000) is the reaction product of the N-formyl derivative (900) and the ketalizing agent. More specifically, the ketalizing agent selectively ketalizes the substituent attached to the carbon atom at the C(6) position (e.g., $R_6$ or =O) of the N-formyl derivative (900), forming the ketal (1000) carrying the $R_{66a}$ and $R_{66b}$ substituents.

A variety of ketalizing agents may be used in the above ketalization reaction. In general, the ketalizing agent may be any protecting compound that reacts with the existing substituent attached to the carbon atom at the C(6) position (e.g., $R_6$ or =O) of the N-formyl derivative (900) to form the ketal moiety comprising $R_{66a}$, $R_{66b}$ and the carbon atom to which they are attached (i.e., the C(6) carbon). Suitable ketalizing agents include, for example, alkanols (i.e., a compound having one hydroxy group, such as methanol and ethanol), alkanediols (i.e., a compound having two hydroxy groups), and thiols (i.e., a compound having a sulfhydryl (—SH) group). Preferably, the ketalizing agent is selected from alkanediols and thiols; thus, for example, the ketalizing agent may include 1,2-ethanediol (ethylene glycol), 1,2-ethanedithiol, 1,2-propanediol, 1,3-propanediol, 1,2-propanedithiol, 1,3-propanedithiol, 1,2-butanediol, 1,3-butanediol, 2,3-butanediol, 1,2-pentanediol, 2,4-pentanediol, 2,4-dimethyl-2,4-pentanediol, 1,2-hexanediol, 2-ethyl-1,3-hexanediol, 1,2-octanediol, 1,2-decanediol, 1,2-dodecanediol, cis-1,2-cyclopentanediol, trans-1,2-cyclopentanediol, cis-1,2-cyclooctanediol, trans-1,2-cyclooctanediol, (+)-pinanediol, (−)-pinanediol, catechol, and enantiomers and combinations thereof. In a particular embodiment, the ketalizing agent includes 1,2- and 1,3-alkanediols such as 1,2-ethanediol (ethylene glycol), 1,2-propanediol, 1,3-propanediol, 1,2-butanediol, 1,3-butanediol, combinations thereof, and the like.

The ketalization reaction mixture typically contains from about 2 equivalents to about 8 equivalents of the ketalizing agent for each equivalent of the N-formyl derivative (900); preferably from about 3 equivalents to about 6 equivalents, for example, about 4 equivalents.

The ketalization reaction is preferably carried out in the presence of an acid catalyst. In general, the acid catalyst can assist in controlling the regiochemistry of the β,γ-alkene and can assist in preserving anhydrous conditions. Suitable acid catalysts that may be used include, for example, methanesulfonic acid, p-toluenesulfonic acid, sulfuric acid, phosphoric acid, trifluoroacetic acid, trichloroacetic acid, oxalic acid, boron trifluoride, and combinations thereof. Alternatively, lithium or magnesium salts may be used such as, for example, magnesium triflate or lithium hexafluorophosphate. Regardless of the particular acid catalyst(s) utilized, it is preferably an anhydrous acid catalyst.

The ketalization reaction mixture typically includes from about 0.5 equivalents to about 5 equivalents of the acid catalyst for each equivalent of the N-formyl derivative (900); preferably from about 0.5 equivalents to about 1 equivalent.

Where the ketalizing agent is employed as the liquid composition for formylating agent removal (described above), the acid catalyst is preferably added to the reaction mixture after the removal of the formylating agent from the formylation product mixture. That is, the ketalizing agent having a boiling point greater than the boiling point of the formylating agent is added to the formylation product mixture (or the formylation reaction is carried out in the presence of the ketalizing agent) and the product mixture is heated to a temperature in excess of the boiling point of the formylating agent to remove the formylating agent. Then, the acid catalyst may be contacted with the N-formyl derivative (900) dissolved in the ketalizing agent to assist in the ketalization process.

It has been found that the yields of the desired ketal (1000) can be reduced with the presence of water in the reaction mixture; thus, the ketalization reaction is preferably performed under anhydrous conditions. Conventional methods for obtaining anhydrous conditions, such as molecular sieves, anhydrous salts, and Dean-Stark traps, for example, are generally effective. In a particular embodiment, the ketalization reaction is performed in the presence of a water scavenger. In general, the water scavenger is a compound or mixture of compounds that react with, remove, and/or bind irreversibly with water in the reaction system. The water scavenger may be added separately from the other components of the reaction mixture or, alternatively, it may be pre-mixed with one of the components and the mixture is then combined with the remaining components.

A variety of water scavengers may be utilized, provided that the presence of the water scavenger does not adversely affect the ketalization reaction. Suitable water scavengers include, but are not limited to, compounds corresponding to the formula: $R_YC(OR_Z)_3$, wherein $R_Y$ is hydrogen or hydrocarbyl and $R_Z$ is hydrocarbyl. Preferably, $R_Y$ is hydrogen or alkyl and $R_Z$ is alkyl; in this embodiment, for example, the water scavenger may correspond to trimethoxymethane, trimethoxyethane, trimethoxypropane, trimethoxybutane, trimethoxypentane, triethyoxyethane, triethoxypropane, combinations thereof, and the like. Alternatively, the water scavenger may be a desiccant such as anhydrous inorganic salts that can form hydrates, e.g., magnesium sulfate ($MgSO_4$) or sodium sulfate ($Na_2SO_4$). Desiccants, however, are generally less preferred due to their tendency to form a suspension in the reaction mixture.

The ketalization reaction mixture typically includes from about 0.2 equivalents to about 4.0 equivalents of the water scavenger for each equivalent of the N-formyl derivative (900), or more, depending on the amount of water present in the reaction mixture. Typically, the ketalization reaction mixture includes from about 1 equivalent to about 2 equivalents of the water scavenger for each equivalent of the N-formyl derivative (900).

The ketalization reaction is preferably carried out in the presence of the same liquid composition utilized in Stage 1 to assist in the removal of the formulating agent (i.e., the liquid composition having a boiling point that is greater than the boiling point of the formylating agent). Stated another way, the N-formyl derivative (900) may be subjected to the ketalization reaction without an intermediate crystallization of the N-formyl derivative (900) after the Stage 1 formylation reaction.

In addition to the liquid composition having a boiling point that is greater than the boiling point of the formylating agent, one or more additional solvents may be present in the ketalization reaction mixture. Depending on the temperature of the formylation product mixture (i.e., after the formylation reaction itself and/or after the removal of the formylating agent by heating), a water immiscible solvent may be included in the ketalization reaction mixture before or after cooling the reaction mixture and/or before adding the ketalizing agent, acid catalyst, and/or the water scavenger. For instance, the formylation product mixture described above in Stage 1 is typically cooled (e.g., to about 40-50° C.) prior to combination with the ketalizing agent, acid catalyst, and/or water scavenger. A water immiscible solvent may then be added to the final formylation product mixture to assist in maintaining the homogeneity of the formylation product mixture containing the N-formyl derivative (900) prior to ketalization and/or to facilitate the transfer from one reaction stage to the next without an intermediate crystallization. Similarly, where the N-formyl derivative (900) is crystallized from the formylation product mixture following the Stage 1 formylation reaction, the N-formyl derivative (900) may be resolubilized using a variety of water immiscible solvents prior to ketalization.

Upon cooling, the formylation product mixture containing the N-formyl derivative (900) may form a thick suspension. Thus, the water immiscible solvent is typically added after cooling the formylation product mixture and prior to reacting the N-formyl derivative (900) with the ketalizing agent, the acid catalyst, and/or the water scavenger to form a relatively homogeneous mixture; alternatively, however, the water immiscible solvent may be combined with one or more of these reactants and added to the formylation product mixture. Exemplary water immiscible solvents that may be used include, but are not limited to, chloroform, dichloromethane, 1,2-dichloroethane, chlorobenzene, xylene, diethyl ether, ethyl acetate, propyl acetate, tetrahydrofuran, combinations thereof, and the like. In a particular embodiment, the water immiscible solvent is chloroform.

The ketalization reaction is typically conducted under an inert atmosphere (e.g., nitrogen or argon) at ambient pressure; preferably, the reaction is carried out in a nitrogen atmosphere. The reaction temperature for the ketalization reaction is typically from about −10° C. to about 30° C.; preferably, the reaction temperature is from about 0° C. to about 10° C. The duration of the ketalization reaction is generally from about 0.5 hours to about 3 hours; preferably about 1 hour.

Completion of the ketalization reaction may be monitored by conventional methods (e.g., TLC, HPLC). After the formation of the ketalization product mixture by the conversion of the N-formyl derivative (900) to the ketal (1000), the ketalization product mixture containing the ketal (1000) and the liquid composition having a boiling point that is greater than the boiling point of the formylating agent may be directly utilized in Stage 3 of Reaction Scheme 1 (i.e., the halogenation reaction described in further detail below) without an intermediate crystallization of the ketal (1000). Alternatively, the ketal (1000) may be crystallized from the ketalization product mixture according to conventional methods.

Halogenation of a Ketal (1000) to Form a Haloketal (1100)

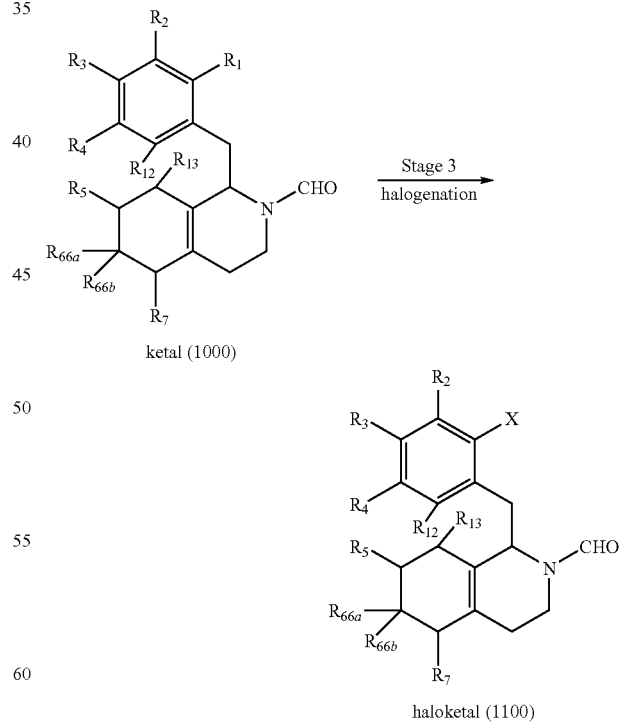

As illustrated in Reaction Scheme 4, Stage 3 involves the reaction of a ketal (1000) with a halogenating agent to form a haloketal (1100), wherein $R_1$, $R_2$, $R_3$, $R_4$, $R_5$, $R_{66a}$, $R_{66b}$, $R_7$, $R_{12}$, $R_{13}$, and X are as defined in connection with Formulae (800), (900), (1000), and/or (1100) above. The haloketal (1100) is the reaction product of the ketal (1000) and the halogenating agent. In particular, the ketal (1000) is selectively halogenated at the C(1) position to form the haloketal (1100).

A variety of halogenating agents may be used in the selective halogenation reaction of Stage 3. Suitable halogenating agents that may be used include, for example, chlorine ($Cl_2$), bromine ($Br_2$), N-bromoacetamide (NBA), N-bromosuccinimide (NBS), 1,3-dibromo-5,5-methylhydantoin (DBDMH), 1,3-dichloro-5,5-methylhydantoin (DCDMH), N-chlorosuccinimide (NCS), pyridinium tribromide, and the like. Chlorine ($Cl_2$) and bromine ($Br_2$), while effective as halogenating agents in this stage, are generally less preferred due to their undesirable tendency to form hydrogen halides (i.e., hydrochloric acid, hydrobromic acid) in the reaction mixture. In a particular embodiment, the halogenating agent is selected from N-bromoacetamide (NBA), N-bromosuccinimide (NBS), and combinations thereof; in this embodiment, N-bromosuccinimide (NBS) is particularly preferred since it is relatively inexpensive and is commercially available from a variety of sources.

The halogenation reaction mixture typically contains from about 0.9 equivalents to about 1.1 equivalents of the halogenating reagent for each equivalent of the ketal (1000); preferably from about 0.95 equivalents to about 1.05 equivalents, for example, from about 1.0 equivalents to about 1.05 equivalents. Depending on the halogenating agent, however, greater or less equivalents may be used. For example, NBA and NBS are typically used in the above equivalent ranges, while about half as many equivalents of DBDMH (0.5 to 0.51 equivalents) are typically used for each equivalent of the ketal (1000).

The halogenation reaction is preferably carried out in the presence of the same liquid composition utilized in Stage 1 and 2 (i.e., the liquid composition having a boiling point that is greater than the boiling point of the formylating agent). Stated another way, the ketal (1000) may be subjected to the halogenation reaction without an intermediate crystallization of the N-formyl derivative (900) after the Stage 1 formylation reaction and/or without an intermediate crystallization of the ketal (1000) after the Stage 2 ketalization reaction. In addition to the liquid composition utilized in the formylating agent removal in Stage 1 or Stage 2, other solvents may also be present, e.g., to solubilize one or more of the starting compounds in Stages 1, 2, and/or 3 (i.e., hexahydroisoquinoline (800), N-formyl derivative (900), and/or ketal (1000)), and/or to facilitate the transfer from one reaction stage to the next without an intermediate crystallization, as described above.

It has been found that the presence of water in the reaction mixture can result in the undesirable formation of α,β-ketone compounds by way of hydrolysis of the ketal (1000). Further, the α,β-ketone compounds formed by hydrolysis may undergo undesirable α-halogenation (i.e., the halogenation of the $R_7$ substituent). As such, the halogenation reaction is preferably performed under anhydrous conditions. As discussed above, conventional methods (e.g., molecular sieves, Dean-Stark traps) may be utilized to maintain anhydrous conditions. Preferably, the halogenation reaction is performed in the presence of a water scavenger as described above (e.g., using $R_YC(OR_Z)_3$, wherein $R_Y$ is hydrogen or hydrocarbyl and $R_Z$ is hydrocarbyl). Desiccants (e.g., $MgSO_4$ or $Na_2SO_4$) may also be utilized, but are generally less preferred for the reasons described above.

The halogenation reaction mixture typically includes from about 0.2 equivalents to about 4.0 equivalents of the water scavenger for each equivalent of the ketal (1000), or more, depending on the amount of water present in the reaction mixture. Typically, the halogenation reaction mixture includes from about 0.5 equivalents to about 1.0 equivalents of the water scavenger for each equivalent of the ketal (1000).

The halogenation reaction may also take place in the presence of an acid. For example, the ketalization product mixture used as the starting substrate for the halogenation reaction may contain excess or unreacted acid catalyst from the ketalization reaction described above. Thus, the halogenation reaction mixture may contain, for example, sulfuric acid, phosphoric acid, methanesulfonic acid, p-toluenesulfonic acid, trifluoroacetic acid, trichloroacetic acid, oxalic acid, boron trifluoride, and combinations thereof.

Selective halogenation of the ketal (1000) is typically conducted under an inert atmosphere (e.g., nitrogen or argon) and at ambient pressure; preferably, the reaction is carried out in a nitrogen atmosphere. The reaction temperature for the halogenation reaction is typically from about −60° C. to about 20° C.; more typically from about −30° C. to about 20° C.; preferably from about −25° C. to about 0° C., for example, from about −25° C. to about −5° C. During the halogenation reaction, however, an exotherm may be noted, e.g., raising the reaction temperature to from about 0° C. to about 5° C. The halogenation reaction generally occurs relatively rapidly, with reaction times ranging anywhere from several minutes to several hours depending on the particular reagents and equipment utilized and the scale of the reaction.

Completion of the halogenation reaction may be monitored by conventional methods (e.g., TLC, HPLC).

Once the halogenation reaction is complete or has proceeded as long as desired, the resulting halogenation product mixture comprising the haloketal (1100) may be subjected to an aqueous/organic extraction to remove by-products and other impurities. In general, conventional aqueous/organic extraction techniques may be utilized. In a particular embodiment, an aqueous solution comprising water is added to the halogenation product mixture, followed by the addition of an organic extraction solvent. Alternatively, the organic extraction solvent may be added to the halogenation product mixture first, followed by the addition of the aqueous solution; or, the aqueous solution and the extraction solvent may be added to the halogenation product mixture simultaneously. Preferably, the extraction is carried out at a pH of greater than about 2 to help prevent migration of the β,γ-ketone to an α,β-ketone. For example, a base may be added to the halogenation product mixture before or after the addition of the aqueous solution comprising water; alternatively, the base may be added to the halogenation product mixture before or after the addition of the organic extraction solvent. By way of another alternative, the aqueous solution comprising water may further comprise a base. Suitable bases include, but are not limited to, organic bases such as substituted or unsubstituted pyridine, N-methyl morpholine, trialkylamines such as trimethylamine or triethylamine (TEA), and the like.

The organic extraction solvent preferably has a boiling point that is less than the boiling point of the water soluble solvent added to halogenation product mixture following extraction (described in further detail below). Suitable organic extraction solvents include, for example, chloroform, dichloromethane, chlorobenzene, 1,2-dichloroethane, ethyl acetate, and combinations thereof. In a particular embodiment, the organic extraction solvent is chloroform. The combination of the halogenation product mixture, the aqueous solution, and the extraction solvent results in the formation of a mixture containing a solvent portion and an aqueous portion. The solvent portion generally includes the organic extraction solvent and any other solvents previous present in the halogenation product mixture (e.g., a solvent used in the removal of the formylating agent in Stage 1), and also includes the desired haloketal (1100). The aqueous portion, which is subsequently discarded, generally includes the aqueous solution components (e.g., water), base, by-products of the reacted halogenating agent, and undesirable water soluble components such as reaction by-products and other impurities. Separation of the solvent portion and the aqueous portion may be carried out by conventional means such as a separatory funnel or cannula. Extraction of the halogenation product mixture can be carried out multiple times and the successive organic layers combined to maximize recovery of the haloketal (1100).

In some embodiments, the hydrolyzation reaction in Stage 4 of Reaction Scheme 1 described below takes place in the presence of a water soluble solvent. Accordingly, the liquid composition used in the formylating agent removal and generally present in the formylation, ketalization, and/or halogenation product mixtures is preferably separated from the formylation, ketalization, or halogenation product mixtures using a water soluble solvent. This separation is generally accomplished by including in the formylation, ketalization, or halogenation product mixtures a water soluble solvent having a boiling point that is greater than the boiling point of the liquid composition. In addition to the liquid composition, other solvents and reactants having lower boiling points than the boiling point of the water soluble solvent that may be present in the various product mixtures may be separated from the product mixtures as well. In general, the removal of these components and replacement of the same with a water soluble solvent may be carried out, for example, after removal of the formylating agent in Stage 1, after the ketalization reaction in Stage 2, or after the halogenation reaction in Stage 3; preferably, separation of the liquid composition is carried out after the halogenation reaction in Stage 3 (i.e., the liquid composition is separated from the halogenation product mixture).

In general, any water soluble solvent may be utilized, provided that the boiling point of the water soluble solvent is greater than the boiling point(s) of the other components to be removed in favor of the water soluble solvent (e.g., the liquid composition and/or other solvents). Typically, the water soluble solvent has a boiling point of from about 80° C. at 1 atm to about 250° C. at 1 atm; preferably from about 100° C. at 1 atm to about 200° C. at 1 atm. As noted above, however, a reduction in the pressure may result in a corresponding reduction in the boiling point of the water soluble solvent and any other solvents. Suitable water soluble solvents include, for example, dimethylformamide (DMF) (boiling point ~153° C. at 1 atm), dimethylsulfoxide (DMSO) (boiling point ~189° C. at 1 atm), dimethylacetamide (DMAC) (boiling point ~165° C. at 1 atm), N-methylpyrrolidinone (NMP) (boiling point ~202° C. at 1 atm), higher boiling alcohols (such as 1-butanol (boiling point ~117.7° C. at 1 atm), 1,2-ethanediol (boiling point ~195° C. at 1 atm), isopropanol (boiling point ~82.4° C. at 1 atm), isobutanol (boiling point ~107° C. at 1 atm), and tert-butanol (boiling point ~82.2° C. at 1 atm)), diethylene glycol dimethyl ether (boiling point ~162° C. at 1 atm), triethylene glycol dimethyl ether (boiling point ~216° C. at 1 atm), and combinations thereof. In a particular embodiment, the water soluble solvent is dimethylformamide (DMF).

Following the addition of the water soluble solvent, the halogenation product mixture/water soluble solvent combination is heated to a temperature in excess of the boiling point of the liquid composition used in the removal of the formylating agent in Stage 1. As described in the formylating agent removal procedure in Stage 1, other components having boiling points that are lower than the boiling point of the water soluble solvent may also be removed during heating. The heating step essentially distills off all or substantially all of the liquid composition used in the removal of the formylating agent in Stage 1 (and other solvents) from the halogenation product mixture, leaving the haloketone (1100) dissolved in the water soluble solvent.

By way of example, the halogenation product mixture may contain chloroform (e.g., as the extraction solvent and/or the solubilizing solvent; boiling point ~61° C. at 1 atm) and propyl acetate (as the solvent used in the removal of the formylating agent in Stage 1; boiling point ~102° C. at 1 atm). Dimethylformamide (as the water soluble solvent; boiling point ~153° C. at 1 atm) can be added to the halogenation product mixture and the resulting combination heated. Heating the combination to a temperature that is above about 102° C. (the boiling point of the propyl acetate), but below about 153° C. (the boiling point of the dimethylformamide), will substantially drive off both the chloroform and the propyl acetate, leaving the dimethylformamide as the predominant solvent in the halogenation product mixture.

The heating step may be carried out in ambient air or in an inert environment (e.g., nitrogen or argon); preferably, the heating step is carried out in a nitrogen atmosphere. Further, the heating step may be conducted under standard pressure (i.e., 1 atm) or, alternatively, the heating step may be conducted under reduced pressure. In general, performing the heating step under reduced pressure is preferable, since the boiling points of the various solvents will be reduced and a relatively lower temperature will be needed to drive off the undesirable lower boiling solvents. Typically, the heating step is carried out at a pressure of from about 0.06 atm (about 45 mm Hg) to about 0.26 atm (198 mm Hg). For example, the heating step may be carried out at a pressure of about 0.08 atm (about 60 mm Hg), about 0.10 atm (about 76 mm Hg), about 0.12 atm (about 91 mm Hg), about 0.14 atm (about 106 mm Hg), about 0.16 atm (about 122 mm Hg), about 0.18 atm (about 137 mm Hg), about 0.20 atm (about 152 mm Hg), about 0.22 atm (about 167 mm Hg), or about 0.24 atm (about 182 mm Hg). If the heating step is carried out at a pressure of from about 0.2 atm to about 0.06 atm, for example, chloroform will typically have a boiling point of from about −6° C. to about 17° C., propyl acetate will typically have a boiling point of from about 19° C. to about 48° C., and dimethylformamide will typically have a boiling point of from about 75° C. to about 103° C.

The product mixture/water soluble solvent combination is typically heated until at least 50% (by volume) of the liquid composition used in the removal of the formylation agent in Stage 1 has been removed. For example, the combination may be heated until about 55% (by volume), about 60% (by volume), about 65% (by volume), about 70% (by volume), about 75% (by volume), about 80% (by volume), about 85% (by volume), about 95% (by volume), or about 99% (by volume) of the liquid composition used in the removal of the formylation agent in Stage 1 has been removed from the system. In a particular embodiment, at least 95% of the liquid composition is removed from the system.

Following removal of the various compositions and/or solvents having lower boiling points than the boiling point of the water soluble solvent, the resulting halogenation product mixture containing the haloketal (1100) and the water soluble solvent may be directly utilized in Stage 4 of Reaction Scheme 1 (i.e., the hydrolyzation reaction described in further detail below) without an intermediate crystallization of the haloketal (1100). Alternatively, the haloketal (1100) may be crystallized from the halogenation product mixture according to conventional methods.

Hydrolysis of a Haloketal (1100) to Form a Haloketone (1200)

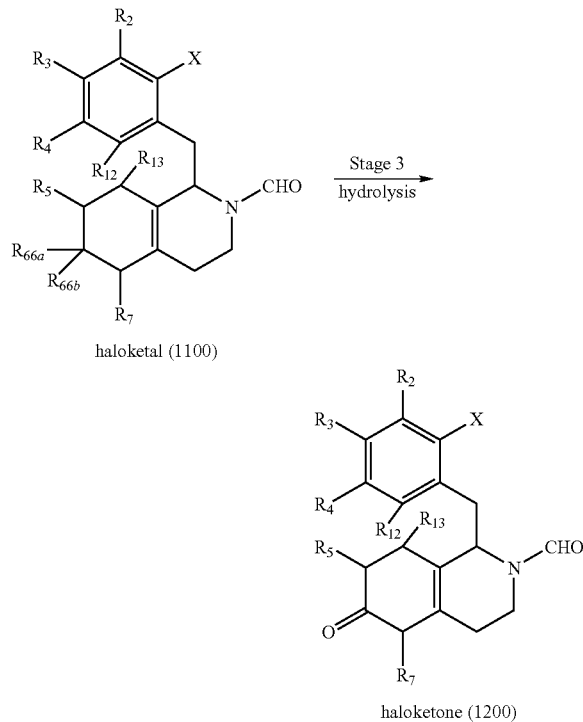

haloketal (1100)

haloketone (1200)

As illustrated in Reaction Scheme 5, Stage 4 involves the reaction of a haloketal (1100) with a hydrolyzing agent to form a haloketone (1200), wherein $R_2$, $R_3$, $R_4$, $R_5$, $R_{66a}$, $R_{66b}$, $R_7$, $R_{12}$, $R_{13}$, and X are as defined in connection with Formulae (800), (900), (1000), (1100), and/or (1200) above. The haloketone (1200) is the reaction product of the haloketal (1100) and the hydrolyzing agent. In general, any hydrolyzing agent that can hydrolyze the $R_{66a}$ and $R_{66b}$ substituents to form a keto moiety at the C(6) position may be utilized. Preferably, the hydrolyzing agent is a relatively mild hydrolyzing agent that will not cause substantial isomerization of the resulting β,γ-unsaturated haloketone (1200), and that will not disturb any other substituents on the polycyclic backbone (i.e., X, $R_2$, $R_3$, $R_4$, $R_5$, $R_7$, $R_{12}$, $R_{13}$, and/or the N-formyl moiety).

Suitable hydrolyzing agents include organic and inorganic acids, bases, and alcohols. In a particular embodiment, the hydrolysis is carried out by a hydrolyzing agent in an aqueous acidic medium (e.g., at a pH of less than 7, less than 6, less than 5, less than 4, less than 3, less than 2, or less than 1). For example, the halogenation product mixture may be combined in an aqueous composition comprising water and the pH of the resulting composition adjusted to less than 1 with the hydrolyzing agent.

Numerous hydrolyzing agents may be used to carry out the hydrolysis such as acetic acid, oxalic acid, formic acid, propanoic acid, butanoic acid, pentanoic acid, benzoic acid, hydrochloric acid, sulfuric acid, methanesulfonic acid, hydrobromic acid, trifluoroacetic acid, and combinations thereof. In one embodiment, the hydrolyzing agent comprises an acid having a $pK_a$ at 25° C. of less than about 5; in this embodiment, for example, the hydrolyzing agent may include a carboxylic acid such as formic acid ($pK_a$ at 25° C.=~3.75), acetic acid ($pK_a$ at 25° C.=~4.76), propanoic acid ($pK_a$ at 25° C.=~4.86), butanoic acid ($pK_a$ at 25° C.=~4.83), pentanoic acid ($pK_a$ at 25° C.=~4.84), benzoic acid ($pK_a$ at 25° C.=~4.19), and combinations thereof. In one embodiment, the hydrolyzing agent includes formic acid. This, for example, the hydrolyzing agent may be 88% formic acid, or 98% formic acid in water (e.g., about 1.0 equivalents of water, or more). Acids having a $pK_a$ of greater than about 5 may also be utilized. Typically, when acids having a $pK_a$ of greater than about 5 are utilized, the reaction mixture is heated to assist in carrying out the hydrolysis. Mineral acids (e.g., HCl, $H_3PO_4$, $H_2SO_4$, etc.) are generally effective as hydrolyzing agents but are generally less preferred, since their use tends to result in the formation of undesirable α,β-ketone compounds.

In various embodiments, the hydrolyzation reaction is carried out in the presence of the water soluble solvent described in Stage 3 above. Advantageously, it has been found that the above-described water soluble solvents (e.g., dimethylformamide (DMF), dimethylsulfoxide (DMSO), dimethylacetamide (DMAC), and N-methylpyrrolidinone (NMP)) possess beneficial diluting and buffering characteristics in the hydrolyzation reaction mixture that assist in the preventing the formation of undesirable α,β-unsaturated ketone compounds. Where the haloketal (1100) is crystallized from the halogenation product mixture following the Stage 3 halogenation reaction, the haloketal (1100) may be resolubilized using a variety of organic solvents in Stage 4, including the water soluble solvent described above.

In various alternative embodiments, the hydrolyzation reaction is carried out in the presence of a water immiscible solvent such as those described above. Where the hydrolyzation is performed on a haloketal (1100) dissolved in a water immiscible solvent, for example, the hydrolyzation may be performed in the presence of a phase transfer catalyst. Generally, the phase transfer catalyst is soluble in both the water immiscible solvent and water. Suitable phase transfer catalysts include, for example, tetrahydrofuran (THF), acetonitrile (ACN), dioxane, and alcohols such as butanol.

Hydrolyzation of the haloketal (1100) is typically conducted under an inert atmosphere (e.g., nitrogen or argon) and at ambient pressure; preferably, the reaction is carried out in a nitrogen atmosphere. The reaction temperature for the hydrolysis reaction is typically from about 5° C. to about 35° C.; preferably from about 15° C. to about 25° C. Reaction times can range from about 0.5 to about 4; preferably about 2.

Completion of the hydrolysis reaction may be monitored by conventional methods (e.g., TLC, HPLC).

Once the hydrolyzation reaction is complete or has proceeded as long as desired, the resulting hydrolyzation product mixture comprising the haloketone (1200) is preferably subjected to an extraction to remove the water soluble solvent, by-products, and other impurities and to provide the haloketone (1200) in a solvent system comprising a water immiscible solvent. Alternatively, however, the water soluble solvent may be removed from reaction products earlier in the synthesis, such as from the formylation, ketalization, or halogenation product mixtures by the same methods described below. In one embodiment, the hydrolyzation is performed in the presence of a water immiscible solvent, and thereafter an aqueous solution containing the aqueous acidic medium and the hydrolyzing agent described above is separated from a water immiscible solvent portion containing the desired haloketone (1200). In another embodiment, the hydrolyzation product mixture comprising the haloketone (1200), the water soluble solvent, and the hydrolyzing agent is combined with an aqueous solution comprising water and a water immiscible solvent.

The aqueous solution comprising water generally serves to further solubilize the water soluble solvent to the extent it was not completely or substantially solubilized by the hydrolyzing agent. Preferably, the water immiscible solvent is added to the hydrolyzation product mixture first, followed by the aqueous solution comprising water. It has been found that by performing the combination in this order, there is less likelihood of rearrangement of the haloketone (1200) product (e.g., from the β,γ-ketone compound to an α,β-ketone compound) and the recovery of the haloketone (1200) is maximized.

In general, any water immiscible solvent(s) that can withstand the Grewe cyclization conditions described in Stage 5 below may be utilized. Suitable water immiscible solvents include, for instance, chloroform, dichloromethane, dichloroethane, combinations thereof, and the like. In a particular embodiment, the water immiscible solvent is chloroform. Similar to the extraction described above in Stage 3, the combination of the hydrolyzation product mixture, the aqueous solution, and the water immiscible solvent results in the formation of a mixture containing a water immiscible solvent portion containing the haloketone (1200) and an aqueous portion comprising solubilized water soluble solvent and other undesirable by-products and impurities. Separation of the water immiscible portion and the aqueous portion may be carried out by conventional means such as a separatory funnel or cannula. Extraction of the hydrolyzation product mixture can be carried out multiple times and the successive water immiscible layers combined to maximize recovery of the haloketone (1200). After one or more extractions, the combined water immiscible layers are typically substantially free of the water soluble solvent; thus, the water immiscible solvent (e.g., chloroform) is the predominant solvent in the hydrolyzation product mixture following the water soluble solvent removal step. If desired, additional washes may be performed to ensure that the hydrolyzation product mixture is substantially free of any undesirable components or solvents that may adversely affect the yield of the Grewe cyclization reaction.

After the extraction, the hydrolyzation product mixture comprising the haloketone (1200) and the water immiscible solvent is preferably dried by contacting the reaction product mixture with a water scavenger such as those described above. The water scavenger may be added separately or, alternatively, it may be pre-mixed with one of the other components in the extraction (e.g., the aqueous solution and/or the water immiscible solvent). The water scavenger may be, for example, a desiccant such as magnesium sulfate ($MgSO_4$) or sodium sulfate ($Na_2SO_4$).

Following removal of water soluble solvent from the hydrolyzation product mixture, the haloketone (1200) in the water immiscible solvent may be directly utilized in Stage 5 of Reaction Scheme 1 (i.e., the Grewe cyclization reaction described in further detail below) without an intermediate crystallization of the haloketone (1200). Alternatively, the haloketone (1200) may be crystallized from the water immiscible solvent according to conventional methods.

Grewe Cyclization of a Haloketone (1200) to Form a Morphinan-6-one (1300)

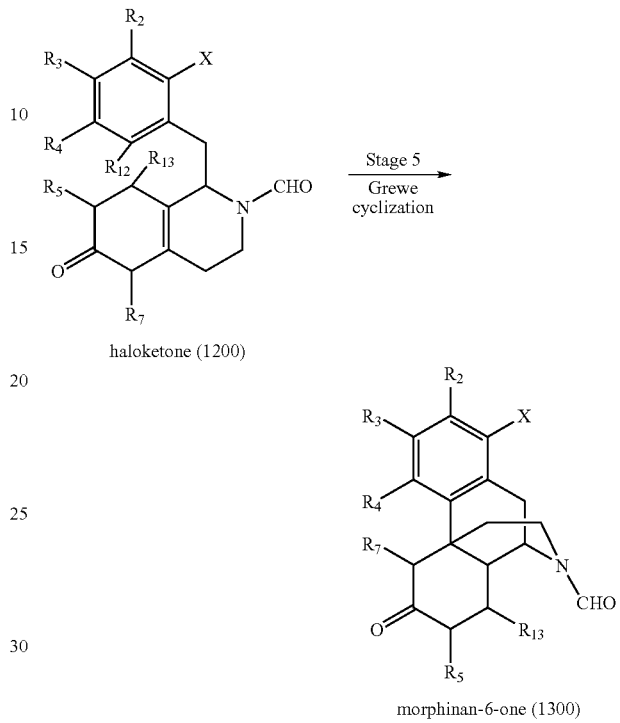

As illustrated in Reaction Scheme 6, Stage 5 involves the transformation of a haloketone (1200) to a morphinan-6-one (1300) under Grewe cyclization conditions, wherein $R_2$, $R_3$, $R_4$, $R_5$, $R_7$, $R_{12}$, $R_{13}$, and X are as defined in connection with Formulae (800), (900), (1000), (1100), (1200), and/or (1300) above. Techniques for transformation of β,γ-bicyclic ketones by Grewe cyclization to form morphinan-6-one products are known in the art (see, e.g., U.S. Pat. Nos. 4,368,326; 4,410,700; 4,521,601; 4,556,712; 4,613,668; and 4,727,146; Beyerman et al., Recl. Trav. Chim. Pays-Bas., 1976, 95, 184; and DeGraw et al., J. Het. Chem., June 1974, 363) and such conventional practices are generally applicable in carrying out the present invention with the modifications as set forth in detail below.

Among other factors affecting the yield of the Grewe cyclization reaction is the acidity of the reaction medium. There is a preferred acidity range that advantageously maximizes the rate of the Grewe cyclization reaction and minimizes the rate of the isomerization of the haloketone (1200) into undesirable α,β-unsaturated morphinan-6-ones. The relative rates of the cyclization and isomerization reactions can be affected by the acidity of the reaction medium, which in turn is affected by the properties of the acid catalyst, the conjugate base of the acid catalyst, the solvent, the substrate, impurities, and additives to the reaction mixture.

Grewe cyclization utilizes a cyclizing acid that catalyzes the reaction. The cyclizing acid may comprise a strong acid, super acid, or combinations thereof. The acid catalyst provides a mixture having sufficient acidity to produce the preferred degree of cyclization. Sufficient acidity of the acid catalyst is primarily determined by the aromatic ring substituents $R_2$, $R_3$, and $R_4$ of the haloketone (1200). In general, electron donating groups will allow the use of less acidic media for rapid cyclization, one or more neutral or electron withdrawing groups will necessitate the use of super acids. Suitable strong acids are those that are completely ionized in solution, usually water in the case of protic acids. Exemplary strong acids include, but are not limited to, benzenesulfonic acid, hydrochloric acid, hydrogen fluoride, fluorosulfonic acid, chlorosulfonic acid, hydrobromic acid, hydroiodic acid, methanesulfonic acid, nitric acid, phosphoric acid, polyphosphoric acid, sulfuric acid, trichloroacetic acid, trifluoroacetic acid, p-toluenesulfonic acid, and combinations thereof. A preferred cyclizing strong acid comprises sulfuric acid.

Typically, it is preferred to employ a super acid as the cyclizing acid in order to obtain the desired degree and rate of cyclization of the haloketone (1200). Super acids include all protic acids that are stronger than 100% sulfuric acid. Suitable super acids include, but are not limited to, anhydrous hydrogen fluoride, fluorosulfonic acid, perchloric acid, perfluoroalkylsulfonic acids (e.g., perfluoro-1-octanesulfonic acid and trifluoromethanesulfonic acid) and combinations thereof or combinations with one or more Lewis acids such as antimony pentafluoride, boron trifluoride, phosphorous pentafluoride, and tantalum (V) fluoride. Some combinations of strong acids with super acids may also provide a mixture of sufficient acidity to produce the preferred degree of cyclization, including, for example, sulfuric or polyphosphoric acid combined with trifluoromethanesulfonic acid and/or fluorosulfonic acid. It may also be possible to employ certain inorganic solids of the general formula $M_xO_y$ as a super acid in catalyzing the Grewe reaction, such as sulfated oxides of zirconium (IV), titanium (IV), iron, molybdenum, tungsten, tin (IV), lanthanum and combinations thereof, optionally supported on silica and/or alumina substrates. Polymeric bound acids such as perfluorinated ion exchange polymers (e.g., NAFION® acidic resin available from DuPont Co.) optionally in combination with other super acids can be used. Preferably, the cyclizing acid is a super acid and comprises trifluoromethanesulfonic acid.

The super acid concentration or strong acid concentration in the Grewe cyclization reaction mixture varies depending on the identity of the acid used. For example, the acid concentration range can be from about 2 equivalents to about 12 equivalents based on the concentration of the haloketone (1200); preferably, from about 6 equivalents to about 10 equivalents.

Preferably, the Grewe cyclization reaction is conducted under an inert atmosphere (e.g., nitrogen or argon); more preferably, the reaction is carried out in a nitrogen atmosphere. The reaction temperature for the Grewe cyclization reaction is preferably maintained below about 15° C.; more preferably from about −10° C. to about 15° C., and even more preferably from about −5° C. to about 5° C. as the cyclizing acid and the haloketone (1200) are being mixed.

The Grewe cyclization reaction is preferably performed in the presence of a cyclization additive. In general, the cyclization additive can improve yield and reproducibility in the Grewe reaction by affecting the properties of the Grewe cyclization reaction mixture. For example, the cyclization additive may reduce the concentration of water in the cyclization reaction mixture as the haloketone (1200) is transformed to the morphinan-6-one product. The reduction or elimination of water effectively increases the acidity of the overall reaction medium. Optimally, cyclization additives are selected so as to react with any water present and form an acid that may be subsequently utilized in catalyzing the Grewe reaction. Suitable cyclization additives generally include acid anhydrides, including gaseous sulfur trioxide, solid phosphorus pentoxide, and combinations thereof. Anhydrous molecular sieves compatible with the super acid media may also be used. Additionally or alternatively, the use of water scavengers in the preceding stages (e.g., Stage 1, 2, 3, and/or 4 above) may function to reduce the presence of water in the cyclization reaction mixture.

The acid anhydrides used may comprise any anhydride of the cyclizing strong and super acids noted above. For example, the acid anhydride may be methanesulfonic anhydride, sulfur trioxide or solutions thereof in sulfuric acid (i.e., fuming sulfuric acid oleums), phosphorous pentoxide or mixtures of phosphorous pentoxide in phosphoric acid (i.e., polyphosphoric acid), trifluoroacetic anhydride, trifluoromethanesulfonic anhydride, and combinations thereof. When a gaseous anhydride is used (e.g., $SO_3$), fuming sulfuric acid is added to the reaction medium. Use of the corresponding acid anhydride not only aids in reducing the concentration of water in the Grewe reaction mixture that may lead to undesired side reactions, but the acid anhydride reacts with any water present and produces additional strong or super acid thereby reducing the cyclizing acid demands. In a particular embodiment, the cyclizing acid and the acid anhydride are trifluoromethanesulfonic acid and trifluoromethanesulfonic anhydride, respectively.

The cyclization additive such as an acid anhydride is used to reduce the water concentration in the cyclization reaction mixture and inhibit potential yield-reducing side reactions. Water may be introduced into the Grewe reaction mixture from several sources including the cyclizing acid catalyst, the source of the haloketone (1200) (i.e., the hydrolyzation product mixture), as well as the solvent(s) in which the reaction(s) take place.

The Grewe cyclization reaction is preferably carried out in the presence of the water immiscible solvent used in the removal of the water soluble solvent in Stage 4. Where the haloketone (1200) is crystallized from the hydrolyzation reaction mixture following the Stage 4 hydrolyzation reaction, the haloketone (1200) may be resolubilized using a variety of organic solvents in Stage 5. In this case, the haloketone (1200) is preferably combined with the organic solvent prior to contacting the cyclizing acid to form the Grewe reaction mixture. Suitable organic solvents are selected from the group consisting of chloroform, dichloromethane, methyl sulfone, tetramethylene sulfone, and combinations thereof. Preferably, the organic solvent comprises chloroform. If the suitable organic solvent forms an azeotrope with water then part or all of the solvent with water may be removed by distillation. Further, the organic solvent is preferably selected to be of a grade that does not include ethanol as a stabilizer since the presence of ethanol, like water, is believed to have an adverse impact on the selectivity of the Grewe reaction.

Preferably, the hydrolyzation product mixture comprising haloketone (1200) and the water immiscible solvent is heated (e.g., at a temperature less than about 60° C.) under vacuum for several days to reduce the concentration of water present. Additionally or alternatively, a water scavenger such as those described above may be added to the hydrolyzation product mixture.

The cyclizing acid may be combined with the acid anhydride prior to being used in the Grewe cyclization reaction, or the acid anhydride and the cyclizing acid may be added to the reaction mixture separately. Preferably, the amount of acid anhydride used is in slight excess relative to the water concentration such that substantially all of the water present in the reaction mixture reacts with the acid an hydride with additional acid anhydride remaining in the reaction mixture to react with any additional water that may happen to be introduced to the reaction mixture (e.g., upon introduction of the haloketone (1200) and/or other solvents to the reaction mixture).

When an acid anhydride is used as the cyclization additive, it typically has a much lower boiling point than the corresponding cyclizing acid. For example, the boiling point of trifluoromethanesulfonic anhydride is about 81-83° C. at 1 atm, while the boiling point of trifluoromethanesulfonic acid is about 167-170° C. at 1 atm. Accordingly, in such an embodiment, the acid anhydride is preferably added to the cyclizing acid and the mixture continuously refluxed while monitoring the vapor temperature of the mixture. As the acid anhydride is added to the cyclizing acid, any water present reacts with the anhydride to form the corresponding acid. The acid anhydride is added until a marked decrease in the vapor temperature of the refluxing mixture is observed, indicating that the amount of acid anhydride added to the mixture is sufficient to substantially react with any water present in the mixture and that excess acid anhydride is present in the mixture. Typically, the acid anhydride is added until the vapor temperature of the refluxing acid and anhydride mixture decreases at least about 20° C. below the original vapor temperature of the refluxing acid prior to addition of the acid anhydride. Any acid anhydride distilled from the refluxing mixture during this treatment may be recovered for reuse.

Generally, the amount of excess acid anhydride present in the Grewe cyclization reaction mixture is from about 1 wt. % to about 20 wt. % based on the total weight of haloketone (1200), the cyclizing acid, the acid anhydride, and the solvent.

In order to maintain the desired reaction temperature as discussed above during Grewe transformation of the haloketone (1200), the mixture of the cyclizing acid and excess acid anhydride is preferably cooled, typically below about 15° C. (e.g., from about −5° C. to about −10° C.) before being combined with the hydrolyzation product mixture comprising the haloketone (1200) and the water immiscible solvent to form the Grewe reaction mixture. Typically, the hydrolyzation product mixture comprising the haloketone (1200) and the water immiscible solvent is added to the cooled mixture of cyclizing acid and remaining acid anhydride at a continuous rate while agitating the resulting Grewe reaction mixture. For example, the hydrolyzation product mixture may be added to the cyclizing acid and acid anhydride mixture over a period from about 10 to about 60 minutes.

Excess anhydride or other cyclization additive present in the cyclizing acid is available to reduce or eliminate any water present in the hydrolyzation product mixture when combined to form the Grewe reaction mixture. Acid anhydride or other cyclization additive may be initially or additionally introduced into the Grewe cyclization reaction mixture. It is preferred to have the acid anhydride present when the cyclizing acid and haloketone (1200) are initially combined. In any event, since the reaction of water and acid anhydride or other cyclization additive can be highly exothermic, proper measures should be employed to cool the Grewe reaction mixture as needed to maintain the desired reaction temperature during the acid-catalyzed transformation of the haloketone (1200) to form the morphinan-6-one (1300).

Once addition of the hydrolyzation product mixture comprising the haloketone (1200) to the cyclizing acid is complete, agitation of the Grewe reaction mixture is continued and the reaction mixture is typically warmed slightly, for example, to a temperature of from about 10° C. to about 25° C. The acid-catalyzed Grewe transformation is allowed to continue for a time sufficient to transform substantially all of the haloketone (1200) to the desired morphinan-6-one (1300) and α,β-unsaturated ketone by-products as determined, for example, by thin-layer chromatography (TLC) or other suitable method. Typically, the duration of the Grewe cyclization reaction after the haloketone (1200) and cyclizing acid reagents have been combined is from about 6 to about 16 hours.

At the conclusion of the Grewe cyclization reaction, the reaction mixture may be quenched. For example, the Grewe reaction mixture may be quenched by adding the reaction mixture to a cooled (e.g., from about −10° C. to about 10° C.) aqueous solvent to ensure that any acid anhydride used as the water scavenger is converted to acid. Preferably, the cooled aqueous solvent has a pH of from about 5 to about 9; more preferably, the cooled aqueous solvent has a pH of about 7.

The cyclization product mixture containing the morphinan-6-one (1300) may be readily recovered from the quenched Grewe reaction mixture using techniques known the art. For example, cyclization product mixture may be extracted from the reaction mixture using the water immiscible solvent (e.g., chloroform) in which the Grewe reaction is conducted. Preferably, the quenched Grewe cyclization reaction is extracted multiple times using an organic solvent to maximize the recovery of the morphinan-6-one product obtained. The organic layers containing the morphinan-6-one (1300) product, any unreacted haloketone (1200) starting compound and other organic components of the Grewe reaction mixture may be combined and further treated to recover additional bicyclic ketone compounds.

The resulting cyclization product mixture containing the morphinan-6-one (1300) may be directly utilized in Stage 6 of Reaction Scheme 1 (i.e., the salt formation reaction described in further detail below) without an intermediate crystallization of the morphinan-6-one (1300). Alternatively, the cyclization product mixture comprising the morphinan-6-one (1300) may be crystallized from the cyclization product mixture according to conventional methods.

Formation of a Morphinan-6-one Salt (1400)

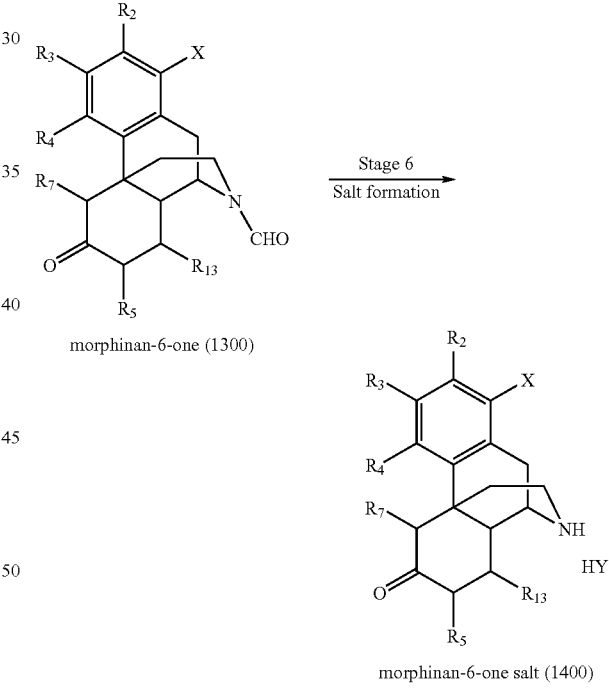

Reaction Scheme 7 morphinan-6-one (1300)

morphinan-6-one salt (1400)

As illustrated in Reaction Scheme 7, Stage 6 involves the formation of a morphinan-6-one salt (1400) from a morphinan-6-one (1300), wherein $R_2$, $R_3$, $R_4$, $R_5$, $R_7$, $R_{13}$, and X are as defined in connection with Formulae (800), (900), (1000), (1100), (1200), (1300), and/or (1400) above. Techniques for the formation of morphinan-6-one salts are generally known in the art, and the Stage 6 reaction may be carried out according to conventional methods (see, e.g., U.S. Pat. Nos. 4,368, 326; 4,410,700; 4,521,601; 4,556,712; and 4,727,146 to Rice). In general, salt formation involves reacting the morphinan-6-one (1300) with an acid or a base to remove (i.e., deprotect) the N-formyl moiety and crystallizing the resulting morphinan-6-one compound as the acid or base salt.

Suitable salts that may be formed include those derived from inorganic or organic acids and bases. Included among such acid salts are the following: acetate, adipate, alginate, aspartate, benzoate, benzenesulfonate, bisulfate, bitartrate, butyrate, citrate, camphorate, camphorsulfonate, cyclopentanepropionate, digluconate, dihydrogen phosphate, dodecylsulfate, ethanesulfonate, fumarate, glucoheptanoate, glycerophosphate, hemisulfate, heptanoate, hexafluorophosphate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, phosphate, picrate, pivalate, propionate, succinate, sulfate, tartrate, tetrafluoroborate, thiocyanate, tosylate, trifluoroacetate, trifluoromethanesulfonate, and undecanoate. Base salts include ammonium salts, alkali metal salts, such as sodium and potassium salts, alkaline earth metal salts, such as calcium, magnesium and zinc salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. In a particular embodiment, the salt is fumarate, tartrate, bitartrate, oxalate, sulfate, bisulfate, phosphate, dihydrogen phosphate, tetrafluoroborate, hexafluorophosphate, methanesulfonate, acetate, trifluoroacetate, trifluoromethanesulfonate, or a hydrohalide salt such as hydrochloride, hydrobromide, or hydroiodide salt (i.e., Y is halo); more preferably in this embodiment, the salt is hydrobromide (i.e., Y is Br⁻). It has been found that hydrohalide salts such as hydrobromide provide a convenient substrate for conventional morphinan-6-one oxide ring closure methods (i.e., the formation of an oxide bridge comprising the $R_4$ and $R_7$ substituents and the carbon atoms to which they are attached), which commonly utilize halogenating agents such as bromine.

Uses of Intermediates

The above-described synthesis stages are important in the preparation of morphinans and analogs thereof. General reaction schemes for the preparation of morphinans are disclosed in U.S. Pat. No. 4,368,326 to Rice, the entire disclosure of which is incorporated by reference. The morphinans and analogs thereof (i.e., the morphinans contain an X group of N—($R_{17}$) or N⁺—($R_{17a}R_{17b}$)) of interest in the practice of the present invention are opiate receptor agonists or antagonists and generally are compounds corresponding to Formula (24)

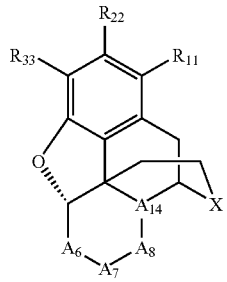

(24)

wherein -$A_6$-$A_7$-$A_8$-$A_{14}$- corresponds to Formulae (S), (T), (U), (V), (W), (X), (Y), or (Z):

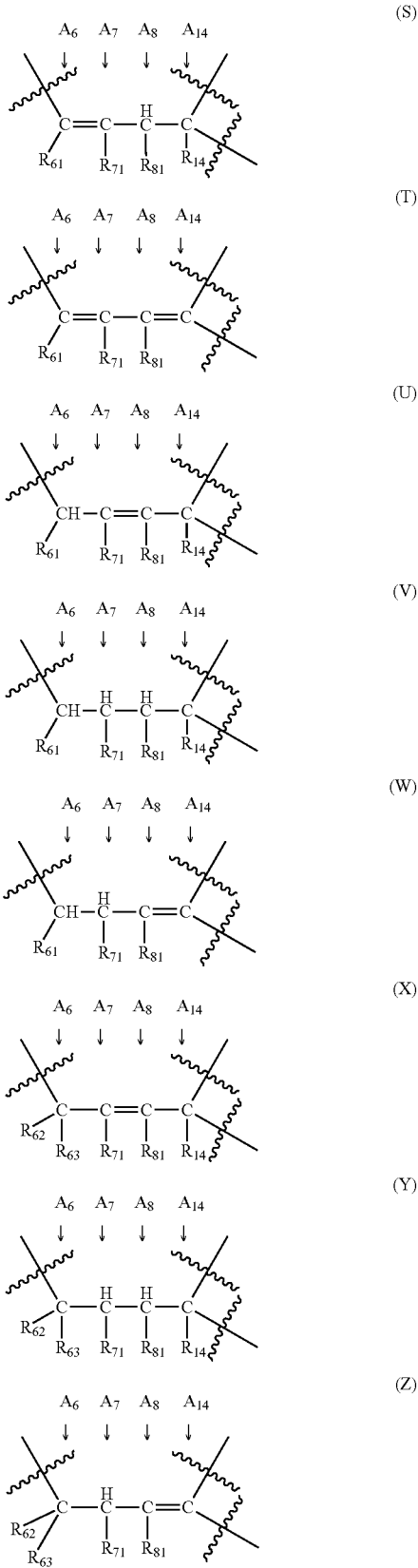

$R_{11}$ and $R_{22}$ are independently hydrogen, substituted and unsubstituted acyl, alkenyl, alkoxy, alkoxyaryl, alkyl, alkylamino, alkylthio, alkynyl, amino, aryl, arylalkoxy, carboalkoxy, carbonyl, carboxyalkenyl, carboxyalkyl, carboxyl, cyano, cyanoalkyl, cycloalkyl, cycloalkylalkyl, cycloalkylether, halo, haloalkoxy, haloalkyl, heteroaryl, heterocyclic, hydroxyalkyl, hydroxy, protected hydroxy, or nitro;

$R_{14}$ is hydrogen, acyloxy, hydroxy, or protected hydroxy;

$R_{17}$ is hydrogen, alkyl, alkoxy, alkylenecycloalkyl, allyl, alkenyl, acyl, formyl, formyl ester, formamide, or benzyl;

$R_{17a}$ and $R_{17b}$ are independently hydrogen, alkyl, cycloalkyl, cycloalkylalkyl, aryl, or benzyl;

$R_{18}$ and $R_{19}$ are independently hydrogen, substituted and unsubstituted acyl, alkenyl, alkoxy, alkoxyaryl, alkyl, alkylamino, arylthio, alkylthio, alkynyl, amino, aryl, arylalkoxy, carboalkoxy, carboxyalkenyl, carboxyalkyl, carboxyl, cyano, cyanoalkyl, cycloalkyl, cycloalkylalkyl, halo, haloalkoxy, haloalkyl, heteroaryl, heterocyclic, hydroxyalkyl, hydroxy, or nitro, or $R_{18}$ and $R_{19}$ together form keto;

$R_{33}$ is alkoxy, acyloxy, hydroxy, or protected hydroxy;

$R_{61}$ is alkoxy, acyloxy, hydroxy, or protected hydroxy;

$R_{62}$ and $R_{63}$ are independently hydrogen, alkyl, alkenyl, alkynyl, allyl, alkoxy, alkylthio, acyloxy, or aryl, together form keto, or together with the carbon atom to which they are attached form a ketal, dithioketal, or monoketal;

$R_{71}$ and $R_{81}$ are independently hydrogen, hydrocarbyl, substituted hydrocarbyl, or halo; and X is oxygen, sulfur, —S(O)—, —S(O$_2$)—, —C(R$_{18}$)(R$_{19}$)—, —N(R$_{17}$)—, or —N$^+$(R$_{17a}$R$_{17b}$)—.

In a particular embodiment, the products and intermediates produced according to the present invention are useful in the preparation of a morphinan compound corresponding to Formula (24) wherein X is —N(R$_{17}$)— and R$_{17}$ is defined as above.

For purposes of clarity, the carbon atoms of Formulae (S), (T), (U), (V), (W), (X), (Y), and (Z) corresponding to A$_6$, A$_7$, A$_8$, and A$_{14}$ of Formula (24), respectively, have been identified (by indicating with an arrow which carbon atom corresponds to each). Further, squiggly lines have been included in Formulae (S), (T), (U), (V), (W), (X), (Y), and (Z) to indicate the points of attachment to the polycyclic ring of Formula (24).

Exemplary morphinans that may be produced according to a variety of methods include, for instance, nordihydrocodeinone (i.e., Formula (24) wherein $R_{11}$, $R_{17}$, and $R_{22}$ are hydrogen, $R_{33}$ is methoxy, X is —N(R$_{17}$)—, and -A$_6$-A$_7$-A$_8$-A$_{14}$- corresponds to Formula (Y) wherein $R_{14}$ is hydrogen, $R_{62}$ and $R_{63}$ together form keto, and $R_{71}$ and $R_{81}$ are hydrogen) (which corresponds to Formula (241) below); dihydrocodeinone (i.e., Formula (24) wherein $R_{11}$ and $R_{22}$ are hydrogen, $R_{33}$ is methoxy, X is —N(R$_{17}$)—, and -A$_6$-A$_7$-A$_8$-A$_{14}$- corresponds to Formula (Y) wherein $R_{14}$ is hydrogen, $R_{62}$ and $R_{63}$ together form keto, and $R_{71}$ and $R_{81}$ are hydrogen) (which corresponds to Formula (242) below); noroxymorphone (i.e., Formula (24) wherein $R_{11}$, $R_{17}$, and $R_{22}$ are hydrogen, $R_{33}$ is hydroxy, X is —N(R$_{17}$)—, and -A$_6$-A$_7$-A$_8$-A$_{14}$- corresponds to Formula (Y) wherein $R_{14}$ is hydroxy, $R_{62}$ and $R_{63}$ together form keto, and $R_{71}$ and $R_{81}$ are hydrogen) (which corresponds to Formula (241) below); and salts, intermediates, and analogs thereof.

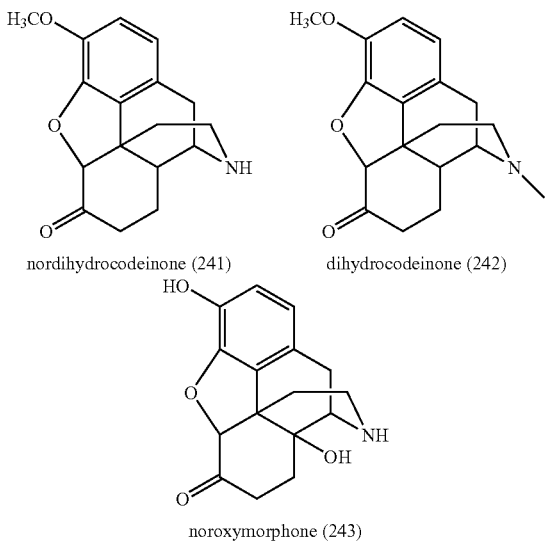

nordihydrocodeinone (241)   dihydrocodeinone (242)

noroxymorphone (243)

DEFINITIONS

The term "acyl," as used herein alone or as part of another group, denotes the moiety formed by removal of the hydroxy group from the group COOH of an organic carboxylic acid, e.g., RC(O)—, wherein R is $R_1$, $R_1$O—, $R_1R_2$N—, or $R_1$S—, $R_1$ is hydrocarbyl, heterosubstituted hydrocarbyl, or heterocyclo, and $R_2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "heteroaryl" as used herein alone or as part of another group denote optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

The terms "hydroxy protecting group" as used herein denote a group capable of protecting a free hydroxy group ("protected hydroxy") which, subsequent to the reaction for which protection is employed, may be removed without disturbing the remainder of the molecule. Exemplary hydroxy protecting groups include ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups for the hydroxy group and the synthesis thereof may be found in "Protective Groups in Organic Synthesis" by T. W. Greene and P. G. M. Wuts, John Wiley & Sons, 1999.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following non-limiting examples are provided to further illustrate the present invention.

Example 1

Synthesis of N-Formyl Derivative (9A) from Hexahydroisoquinoline (8)

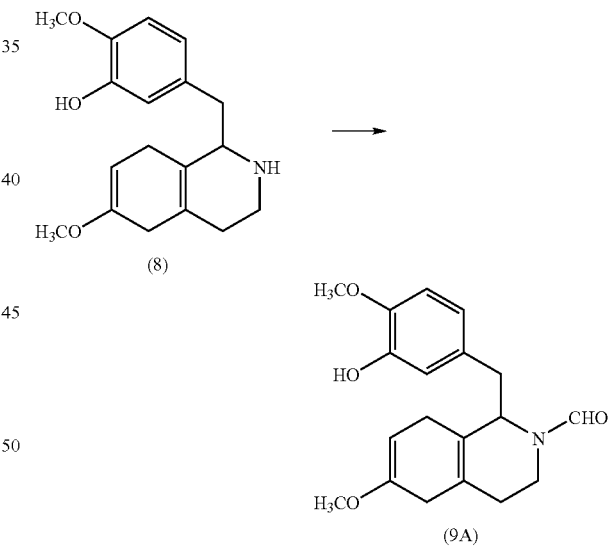

Hexahydroisoquinoline (8) (100 g) was added to propyl formate (700 mL) in a reactor with stirring using a mechanical stirrer. The mixture was heated to reflux for 5 hours. At 2.5 hours, most of the solid was dissolved. K$_2$SO$_4$ (50 g) was then added to the mixture. After stirring for 1 hour, the solids were separated by filtration to give 750 mL of filtrate. The solid was washed with propyl acetate (2×100 mL) affording 950 mL of combined solution. Some of the solvent (~750 mL) was removed by distillation (vapor temperature=82~90° C.). The residue solution was allowed to cool to room temperature.

Chloroform (CHCl$_3$) (550 mL) was added to form a solution of N-formyl derivative (9) in propyl acetate/CHCl$_3$. This solution of N-formyl derivative (9A) in propyl acetate/CHCl$_3$ was ready for the conversion of N-formyl derivative (9A) to ketal (10) in Example 4.

Example 2

Synthesis of N-Formyl Derivative (9A) from Hexahydroisoquinoline (8) (Alternate 1)

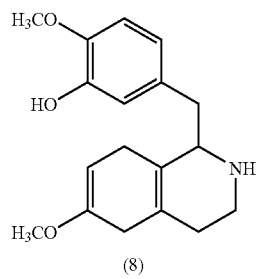

(8)

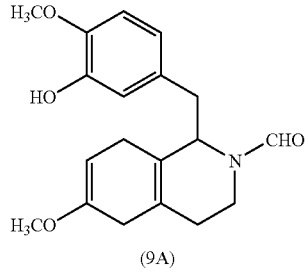

(9A)

To a dried reaction flask under inert atmosphere and stirred mechanically was added hexahydroisoquinoline (8) (59.60 g, 0.20 moles, 1.0 eq) and n-propyl formate (174.23 g, 1.98 moles, 10.0 equivalents). The thick slurry was warmed to 50° C. for one hour, then warmed to 75° C. for an hour, then refluxed for 4 hours. HPLC analysis of a reaction sample indicated that the reaction was complete (0 area % hexahydroisoquinoline (8), 95 area % N-formyl derivative (9A)). Even though a yield of the reaction was not calculated, the conversion was peak (single, hexahydroisoquinoline (8)) to peaks (rotamers, N-formyl derivative (9A)) indicating a quantitative yield. Removal of the by-products and excess n-propyl formate was accomplished by distillation (either atmospheric or reduced pressure) to a thick oil. The residual thick oil was dissolved in anhydrous n-propyl acetate (100 mL), and filtered through a dry glass fritted funnel to clarify the solution. The solution of N-formyl derivative (9A) in n-propyl acetate was ready for the conversion of N-formyl derivative (9A) to ketal (10) in Example 4.

Other products formed in certain experiments yet which were converted in subsequent reactions to ketal (10) included the following:

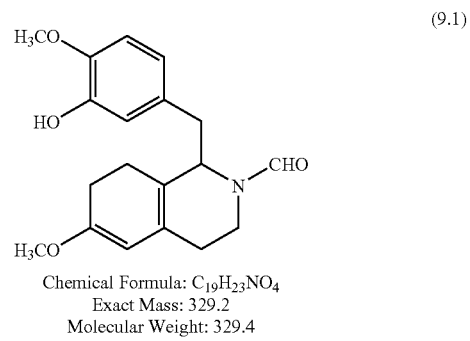

(9.1)

Chemical Formula: C$_{19}$H$_{23}$NO$_4$
Exact Mass: 329.2
Molecular Weight: 329.4

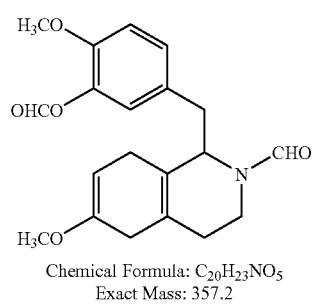

(9.2)

Chemical Formula: C$_{20}$H$_{23}$NO$_5$
Exact Mass: 357.2
Molecular Weight: 357.4

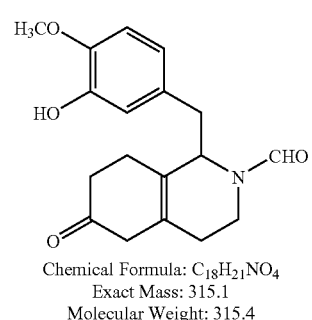

(9.3)

Chemical Formula: C$_{18}$H$_{21}$NO$_4$
Exact Mass: 315.1
Molecular Weight: 315.4

Hexahydroisoquinoline (9.1) generally resulted from excessive heating. This product was rationalized as the thermodynamic product of the reaction, while hexahydroisoquinoline (9) was considered the kinetic product. In some cases, large percentages (up to 70%) were detected. In subsequent reactions, this compound was converted to the ketal (10). Hexahydroisoquinoline (9.2) also resulted from excessive heating and removal of the by-product n-propanol and n-propyl formate. In the subsequent ketalization reaction in Example 4, acid catalysis liberated the free phenol. Hexahydroisoquinoline (9.3) resulted from non-anhydrous reaction conditions. This compound underwent the subsequent ketalization reaction to form ketal (10) at a relatively slow rate.

Other formylation reagents that were utilized according to the same general procedure included 98% formic acid, acetic anhydride, n-ethyl formate, ammonium formate, vinyl formates, and various trialkyl ammonium formates. Another experiment utilized anhydrous ethyl acetate as a solvent.

Example 3

Synthesis of N-Formyl Derivative (9A) from Hexahydroisoquinoline (8) (Alternate 2)

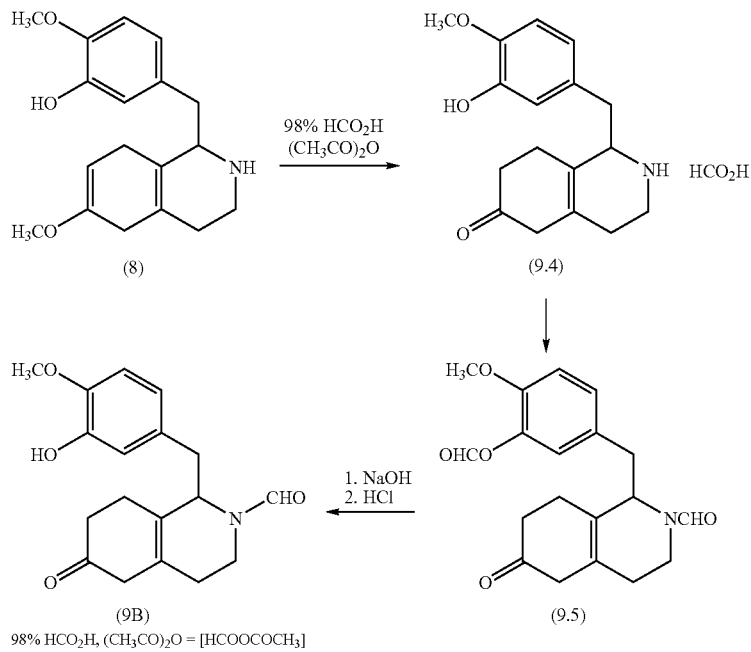

98% $HCO_2H$, $(CH_3CO)_2O$ = [$HCOOCOCH_3$]

Hexahydroisoquinoline (8) (6.15 g, 0.02 moles, 99 area %) was introduced into a flask containing 98% formic acid (70.44 g, 1.52 moles, 5.8 mL) cooled to 5° C. HPLC analysis showed compound (9.4) formed (98 area %). Acetic anhydride (20.83 g, 0.20 moles, 19.3 mL) was added dropwise. The reaction was stirred at room temperature, then warmed to 50° C. for 2 h. HPLC indicated compound (9.5) and compound (9B) formed. The solvent was evaporated under reduced pressure to a thick oil. To this oil was added distilled water (20 mL) and methanol (20 mL). 50% $NaOH/H_2O$ was added until the pH=14.0. This mixture was stirred for 1 h at room temperature. Then 50% $HCl/H_2O$ was added dropwise to pH=3.0. An off white precipitate slowly formed which stood at room temperature for 16 h. The product (9B) (5.97 g, 92% yield) was isolated by filtration, rinsed with distilled water (10 mL), and dried under vac (24 h, 10 mm Hg). Alternatively, compound (9B) was ready for the conversion to ketal (10) in Example 4.

Example 4

Synthesis of Ketal (10) from N-Formyl Derivative (9A)

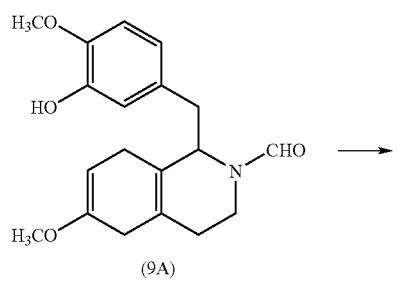

The final solution of Example 1 containing ~0.3328 mol of N-formyl derivative (9A) in propyl acetate/chloroform was cooled to 5° C. Ethylene glycol (55.7 mL) and then $MeSO_3H$ (23.8 mL) was added. The solution was stirred at 5~10° C. for another 40 minutes to form ketal (10). The solution of ketal (10) in propyl acetate/chloroform was ready for the conversion of ketal (10) to haloketal (11) in Example 5.

Example 5

Synthesis of Haloketal (11) from Ketal (10)

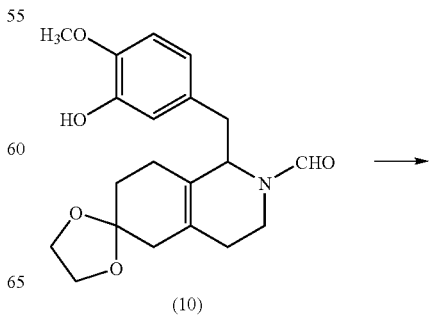

-continued

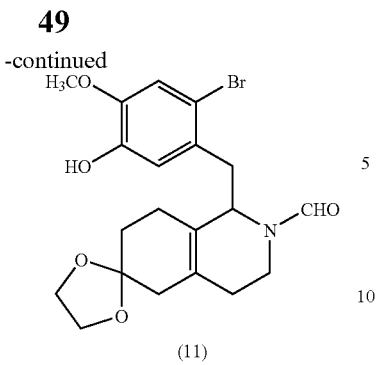

(11)

The final solution of Example 4 containing ketal (10) in propyl acetate/chloroform was further cooled to −20° C. N-bromoacetamide (NBA) (46.0 g) was added in four portions over 45 minutes (15 minutes after each addition) and the reaction temperature maintained between −15° C. and −20° C. Samples were collected for process control at 14 minute intervals after the additions of 23 g and 46 g of NBA. 4.6 g of additional NBA was added based on calculations from the HPLC data of the in-process analysis. After the complete NBA addition, the reaction mixture was stirred at −20° C. for an additional 45 minutes to form haloketal (11). The cooling was then stopped and triethylamine (TEA) (76.5 mL) was added, followed by stirring for 10 minutes and the addition of water (600 mL). The aqueous layer was extracted with CHCl$_3$ (1.0 mL/g). The combined organic layers containing haloketal (11) were washed with water (3×600 mL). The organic solution volume was 650 mL. Some of the solvent (~450 mL) was removed under reduced pressure (0.2 atm~0.11 atm) at 35° C. The vacuum was disconnected and the reactor was filled with nitrogen. The reaction mixture weighted approximately 250 g. Dimethylformamide (DMF) (100 mL) was then added to the solution containing haloketal (11). Most of the solution was distilled at 55° C. under reduced pressure (from 0.2 atm~0.07 atm). The mixture was kept under 0.07 atm for 2 hours after further solvent was removed by distillation. The vacuum was disconnected and the reactor was filled with nitrogen. The reaction mixture weighted approximately 220 g. The solution of haloketal (11) in DMF was ready for the conversion of haloketal (11) to haloketone (12) in the Example 7.

Example 6

Synthesis of Haloketal (11) from Ketal (10)
(Alternate)

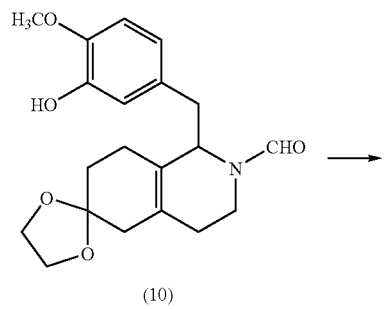

(10)

-continued

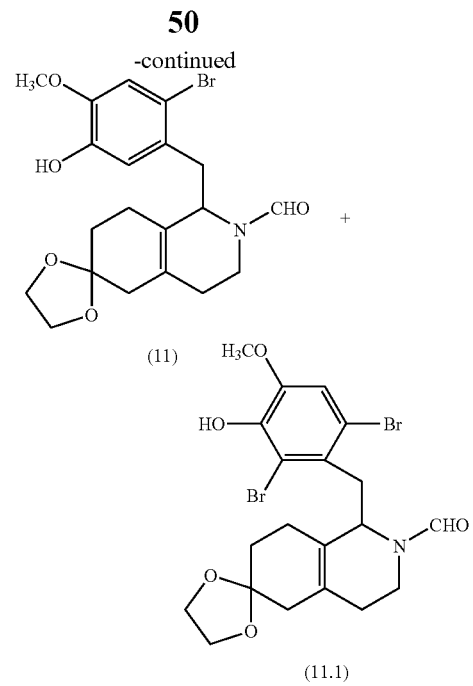

(11)

(11.1)

In the same reaction flask as used in preparation of ketal (10) in the preceding examples, (71.07 g, 0.20 moles, 1.0 eq), dibromodimethylhydantion (28.82 g, 0.10 moles, 0.51 eq.) was added in 4 portions over an hour period maintaining the temperature between −25° C. and −15° C. After each addition, an aliquot was taken and checked by HPLC. Upon completion, the reaction was poured into distilled water (200 mL), stirred for 15 minutes. The aqueous layer was extracted with chloroform (2×100 mL). All the organic layers were combined. The organic layer was washed with distilled water (100 mL), saturated NaCl solution (50 mL), dried over anhydrous MgSO4 (5 g), filtered, then evaporated (distilled) to dryness isolating the product, haloketone (11) as a thick oil. Alternatively, haloketone (11) was ready for the conversion to haloketone (12) in Example 7.

Significant amounts of over-brominated haloketal (11.1) resulted with inappropriate temperature control, insufficient stirring, or excess amounts of brominating agent. The amount of haloketal (11.1) was minimized as much as possible.

Other hydrogenation reagents that were utilized according to the same general procedure included N-bromoacetamide (1.0 eq.) and N-bromosuccinimide (1.0 eq.) Other solvents and reaction temperatures included anhydrous chloroform (−60° C. to −40° C.), dichloromethane (−60° C. to −40° C.), mixtures of propyl acetate (or ethyl acetate) and chloroform (or dichloromethane) (−40° C. to 0° C.), and n-propyl acetate (or ethyl acetate) (0° C. to rt.).

This reaction was also run in anhydrous methanol but the products were slightly different as shown below:

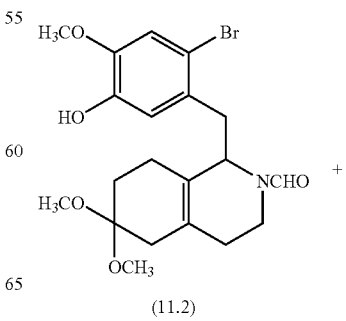

(11.2)

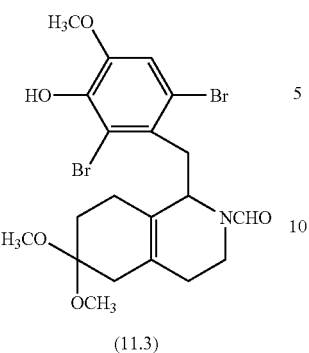

(11.3)

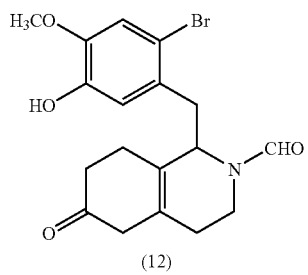

(12)

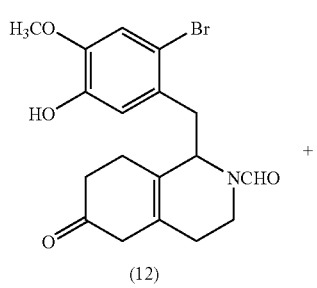

(12)

+

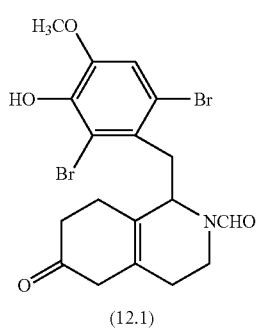

(12.1)

The work-up was also slightly different in the methanol solvent case. Particularly, the reaction was poured into distilled water (100 mL) then extracted with ethyl acetate (3×200 mL). The extracts were combined, washed with distilled water (1×100 mL), saturated NaCl (50 mL), then evaporated to dryness. Small amounts (<1 area %) of compound (12) and (12.1) were obtained.

Example 7

Synthesis of Haloketone (12) from Haloketal (11)

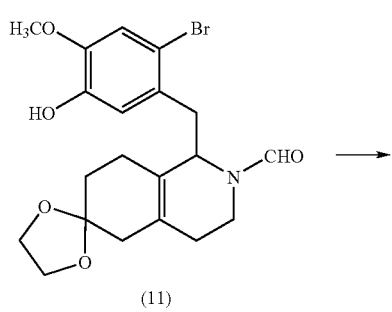

(11)

The final solution of Example 5 containing haloketal (11) in dimethylformamide was cooled to room temperature. A solution of 88% formic acid ($HCO_2H$, 400 mL) was then added. The solution was stirred for about 3 hours to form haloketone (12). $CHCl_3$ (400 mL) and water (800 mL) was added. The aqueous layer was extracted with $CHCl_3$ (200 mL). The combined organic layers were washed with 1% $HCO_2H$ (3×800 mL) and water (800 mL, final wash pH=3.5). The combined organic layers (650 mL) were set aside overnight. No precipitate was formed. Anhydrous $MgSO_4$ (50 g) was added followed by stirring for 2 hours before separation by filtration. The solid was washed with chloroform ($CHCl_3$) (2×50 mL). The combined organic layer was contained in a volume of 720 mL. The solution of haloketone (12) in $CHCl_3$ was ready for the conversion of haloketone (12) to morphinan-6-one (13) in Example 9.

In an alternate procedure, a solution containing haloketal (11) in chloroform ($CHCl_3$) was added to a reactor containing water (1~4 mL per gram of (11)). The resulting solution was agitated and sulfuric acid was added until the pH was less than 1. A phase transfer agent (0.5~2 mL per gram of (11)) was then added. The two phase mixture was stirred for 2-8 hours to form the haloketone (12). The aqueous portion containing the water, sulfuric acid, and solubilized phase transfer catalyst was removed and discarded. The organic layer containing the haloketone (12) was washed with water and extracted, dried over $MgSO_4$, and filtered. The solution of haloketone (12) in $CHCl_3$ was ready for the conversion of haloketone (12) to morphinan-6-one (13) in Example 9.

Example 8

Synthesis of Haloketone (12) from Haloketal (11) (Alternate)

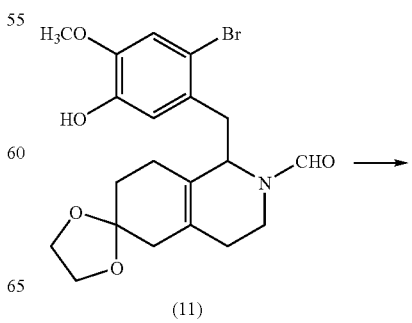

(11)

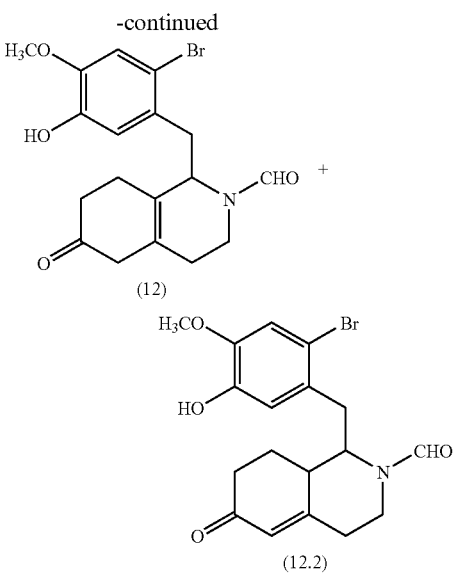

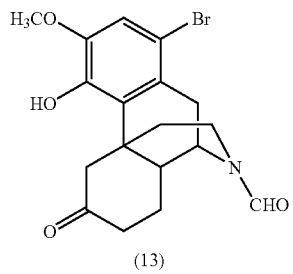

Haloketal (11) from the preceding examples (86.67 g, 0.20 mole, 1.0 eq) was placed in a round bottom flask stirred mechanically in an ice bath (5° C.). To the reaction flask was added 88% formic acid (575 mL) added dropwise over a 30 minute period. Once the addition was complete, the ice bath was removed and the reaction slowly warmed to room temperature. The reaction was followed by HPLC for completeness (1.2 area % compound (11), 85 area % compound (12)). Reaction time was 2 hours. Once the reaction was complete, the mixture was poured into distilled water (1000 mL) and ethyl acetate (1000 mL). The reaction was stirred for 15 minutes at room temperature removing the aqueous layer and discarding. The ethyl acetate layer was washed with distilled water (4×100 mL), saturated NaCl solution (2×50 mL), and dried over anhydrous $MgSO_4$ (~25 g). After filtration and evaporation of the ethyl acetate, a gummy residue of the product, haloketone (12) resulted. The thick oil was dissolved in anhydrous $CHCl_3$ (250 mL) and evaporated to an off white foam. (Weight of haloketone (12) 74.6 g, 85 area %).

Aqueous mineral acids (HCl, $H_3PO_4$, $H_2SO_4$, etc. and other aqueous acids) also produced satisfactory results yet more of compound (12.2) occurred.

Example 9

Synthesis of Morphinan-6-One (13) from Haloketone (12)

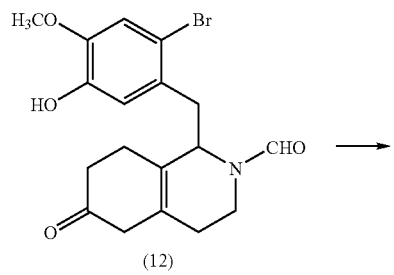

A pre-dried trifluoromethanesulfonic acid ($CF_3SO_3H$, 320 mL) was stirred at 5-10° C. under nitrogen. The final solution of haloketone (12) in $CHCl_3$ (750 mL) from example 7 was added to the acid over 30 minutes to form a two layer mixture. The reaction temperature was kept under 15° C. during the addition. The solution was allowed to warm up to room temperature over 1 hour and stirred at room temperature (22~25° C.) for 21 hours. After this period of time, the stirring was discontinued. Half of the volume of the mixture was transferred into a wash vessel. To the wash vessel was pre-added water (600 mL) and ice (300 g) with stirring. To the reaction vessel, ice cold water (100 mL) was added and stirred for 15 minutes. The mixture was transferred to the wash vessel. The combined materials in the wash vessel were separated into two layers. The organic layer was collected. The aqueous layer (pH=0.25) was extracted with $CHCl_3$ (100 mL). The organic layers were combined to form a solution of about 700 mL.

The combined organic layers (700 mL) were added to a flask. Water (600 mL) was added and stirred (pH=1.35). The reactor was flashed with nitrogen. $Na_3PO_4$ (18 g) was added, dissolved and stirred for 15 minutes (pH=10.95). KOH (50%, 5 mL) was added and stirred for 30 minutes (pH 12.03). The phases were separated. The aqueous layer was 600 mL (pH=11.97) and the organic layer was ~700 mL. The organic layer was washed with $Na_3PO_4$ buffer (3% w/w in water, 600 mL) under nitrogen. The aqueous layer volume was 600 mL (pH=12.02) and the organic layer volume was ~680 mL. The organic layer was again washed with $Na_3PO_4$ buffer (3% w/w in water, 600 mL) under nitrogen. The aqueous layer volume was 600 mL (pH 12.12) and the organic layer volume was ~670 mL. The organic layer was again washed with $HCO_2H$ (3% w/w in water, 600 mL). The aqueous layer volume was 600 mL (pH=2.52) and the organic layer volume was ~670 mL. Since the organic layer was cloudy, it was filtered through a bed of $K_2SO_4$ powder (50 g). The solid was washed with $CHCl_3$ (2×25 mL). The combined organic solution was clear (702 mL). About 450 mL of the solvent was removed by distillation. Methanol (380 mL) was added. The ratio of $CHCl_3$ to methanol was about 1:2. HPLC indicated that the solution contained approximately 92 g of morphinan-6-one (13). The solution of morphinan-6-one (13) in $CHCl_3$/methanol was ready for the conversion of morphinan-6-one (13) to morphinan-6-one salt (14) in Example 10.

Example 10

Synthesis of Morphinan-6-One Salt (14) from Morphinan-6-One (13)

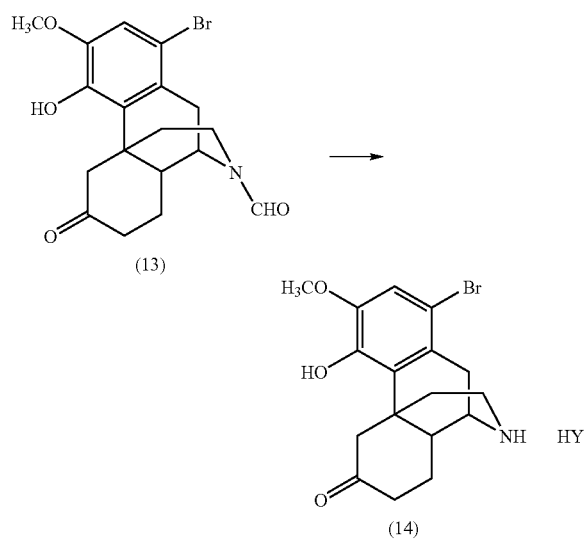

To the solution containing ~92 g of morphinan-6-one (13) in CHCl$_3$/methanol was added concentrated hydrochloric acid (c-HCl, 142.5 mL). Solvent (285 mL) was removed by distillation until the vapor temperature reached about 70° C. After heating to reflux for another 3 hours (reaction temperature=78° C., vapor temperature=73° C.), the HPLC showed that the nitrogen deprotection was complete. The reaction mixture was cooled to room temperature to give a morphinan-6-one solution in HCl/methanol/H$_2$O (~400 mL). Water (950 mL)/CHCl$_3$ (380 mL) were then added with stirring. The pH was adjusted to 8.8-9.2 with concentrated ammonium hydroxide (c-NH$_4$OH) under nitrogen. The aqueous layer was extracted with CHCl$_3$ (2×143 mL) and separated.

The combined organic layers were washed with 1% NH$_4$OH (475 mL, pH 10.52), water (2×475 mL), and filtered through a K$_2$SO$_4$ bed (95 g). The solid was washed with CHCl$_3$ (2×24 mL). To the combined organic solutions (~700 mL) ethanol (300 mL) was added. Most of the solvent was removed by distillation until the vapor temperature reached 70° C. At this point, the majority of the solvent remaining was ethanol (~255 mL solution) from the original CHCl$_3$ solution. Fumaric acid (27.0 g) was then heated under reflux in ethanol (270 mL) to form a clear solution.

The ethanol mixture (254 mL) was added drop-wise to the refluxing solution of fumaric acid in ethanol over 45 minutes. Crystals formed after about one fifth of the ethanolic solution was added. The reflux rate was increased due to the formation of crystals and heat release. The suspension formed was heated to reflux after 1.5 hours after the complete addition. The suspension was cooled to room temperature and then cooled to 0~5° C. for 2 hours.

The crystals were separated by filtration to give 475 mL of solution. The solid was washed with ethanol (2×25 mL). The combined ethanol solutions gave a volume of 525 mL. The solid was further washed with ethyl acetate (2×25 mL). The solid was dried in flowing air for 16 hours to give the fumaric acid salt of morphinan-6-one (14) as a solid (65.65 g).

To prepare the hydrobromide salt of morphinan-6-one (14), the fumaric salt of morphinan-6-one (14) was suspended in chloroform. HBr gas was charged to the suspension until the pH of the suspension is less than about 2 (as tested by wet pH paper), and the suspension was filtered. The filtrate was distilled to remove the chloroform, resulting in the hydrobromide salt of morphinan-6-one (14) as an off-white solid.

In view of the above, it will be seen that the several objects of the invention are achieved and other advantageous results attained.

As various changes could be made in the above processes, products, intermediates, and starting compounds without departing from the scope of the invention, it is intended that all matter contained in the above description shall be interpreted as illustrative and not in a limiting sense.

What is claimed is:

1. A process for the preparation of a ketal (1000), the process comprising converting a hexahydroisoquinoline (800) to a ketal (1000) in a series of steps, the series of steps comprising (a) converting hexahydroisoquinoline (800) to a N-formyl derivative (900) with a formylating agent and (b) converting the N-formyl derivative (900) to the ketal (1000) with a ketalizing agent in the presence of an acid catalyst, whereby the conversion of the hexahydroisoquinoline (800) to the ketal (1000) proceeds without an intermediate crystallization of the N-formyl derivative (900);

wherein the conversion of the hexahydroisoquinoline (800) to the N-formyl derivative (900) produces a formylation product mixture containing the N-formyl derivative (900) and unreacted formylating agent, the unreacted formylating agent being separated from the N-formyl derivative (900) by including in the formylation product mixture a liquid composition having a boiling point that is greater than the boiling point of the formylating agent, and the formylation product mixture being heated to remove unreacted formylating agent and leave the N-formyl derivative (900) dissolved in the liquid composition; and, wherein the hexahydroisoquinoline (800), the N-formyl derivative (900), and the ketal (1000) correspond to Formulae (800), (900), and (1000), respectively:

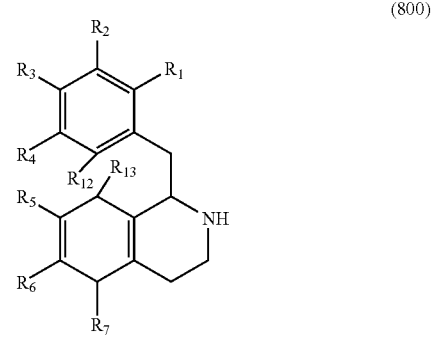

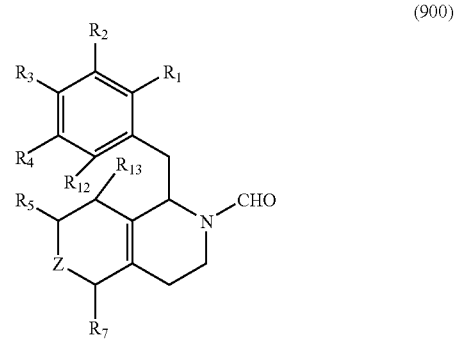

-continued

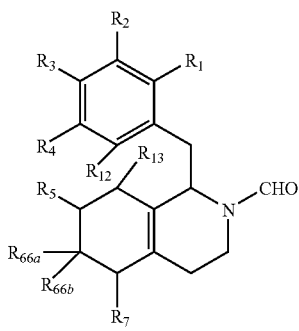
(1000)

wherein:
R$_1$ and R$_7$ are independently hydrogen, hydrocarbyl, substituted hydrocarbyl, or —OR$_{111}$;
R$_5$ is hydrogen, hydrocarbyl, substituted hydrocarbyl, or —OR$_{511}$;
R$_6$ is —OR$_{511}$:
R$_2$ is hydrogen, hydrocarbyl, substituted hydrocarbyl, halo, or —OR$_{211}$;
R$_3$ is hydrogen, hydrocarbyl, substituted hydrocarbyl, or —OR$_{311}$;
R$_4$ is hydrogen, hydrocarbyl, substituted hydrocarbyl, halo, or —OR$_{411}$;
R$_{66a}$ and R$_{66b}$ are independently selected from the group consisting of alkoxy and alkylthio or together with the carbon atom to which they are attached form a ketal, dithioketal, or monothioketal;
R$_{12}$ is hydrogen, hydrocarbyl, substituted hydrocarbyl, halo, or —OR$_{121}$;
R$_{13}$ is hydrogen, hydrocarbyl, substituted hydrocarbyl, halo, or —OR$_{511}$;
R$_{111}$ is hydrogen, hydrocarbyl, substituted hydrocarbyl, or a hydroxy protecting group;
R$_{121}$ is hydrogen, hydrocarbyl, or substituted hydrocarbyl;
R$_{211}$ is hydrogen, hydrocarbyl, substituted hydrocarbyl, or a hydroxy protecting group;
R$_{311}$ is hydrogen, hydrocarbyl, substituted hydrocarbyl, or a hydroxy protecting group;
R$_{411}$ is hydrogen, hydrocarbyl, substituted hydrocarbyl, or a hydroxy protecting group;
R$_{511}$ is hydrogen, hydrocarbyl, substituted hydrocarbyl or a hydroxy protecting group; and
—Z— is

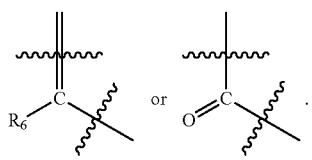

2. The process of claim 1 wherein the liquid composition is a solvent having a boiling point that is greater than the boiling point of the formylating agent.

3. The process of claim 1 wherein the liquid composition is the ketalizing agent.

4. The process of claim 1 further comprising converting the ketal (1000) to a haloketal (1100) with a halogenating agent, whereby the conversion of the ketal (1000) to the halo ketal (1100) proceeds without an intermediate crystallization of the ketal (1000); wherein the haloketal (1100) corresponds to Formula (1100):

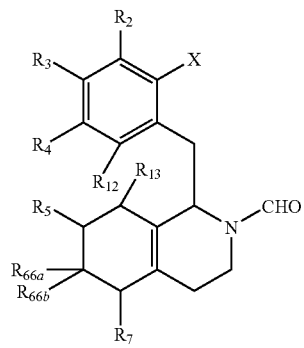
(1100)

R$_2$ is hydrogen, hydrocarbyl, substituted hydrocarbyl, halo, or —OR$_{211}$;
R$_3$ is hydrogen, hydrocarbyl, substituted hydrocarbyl, or —OR$_{311}$;
R$_4$ is hydrogen, hydrocarbyl, substituted hydrocarbyl, halo, or —OR$_{411}$;
R$_5$ is hydrogen, hydrocarbyl, substituted hydrocarbyl, or —OR$_{511}$;
R$_{66a}$ and R$_{66b}$ are independently selected from the group consisting of alkoxy and alkylthio or together with the carbon atom to which they are attached form a ketal, dithioketal, or monothioketal;
R$_7$ is hydrogen, hydrocarbyl, substituted hydrocarbyl, or —OR$_{111}$;
R$_{12}$ is hydrogen, hydrocarbyl, substituted hydrocarbyl, halo, or —OR$_{121}$;
R$_{13}$ is hydrogen, hydrocarbyl, substituted hydrocarbyl, halo, or —OR$_{511}$;
R$_{111}$ is hydrogen, hydrocarbyl, substituted hydrocarbyl, or a hydroxy protecting group;
R$_{121}$ is hydrogen, hydrocarbyl, or substituted hydrocarbyl;
R$_{211}$ is hydrogen, hydrocarbyl, substituted hydrocarbyl, or a hydroxy protecting group;
R$_{311}$ is hydrogen, hydrocarbyl, substituted hydrocarbyl, or a hydroxy protecting group;
R$_{411}$ is hydrogen, hydrocarbyl, substituted hydrocarbyl, or a hydroxy protecting group;
R$_{511}$ is hydrogen, hydrocarbyl, substituted hydrocarbyl, or a hydroxy protecting group; and
X is halo.

5. The process of claim 4 wherein the conversion of the N-formyl derivative (900) to the ketal (1000) produces a ketalization product mixture containing the ketal (1000) in the liquid composition and the conversion of the ketal (1000) to the haloketal (1100) proceeds by treating the ketalization product mixture with a halogenating agent to form a halogenation product mixture containing the haloketal (1100).

6. The process of claim 4 wherein the N-formyl derivative (900) is combined with a water immiscible solvent prior to converting the N-formyl derivative (900) to the ketal (1000) with the ketalizing agent.

7. The process of claim 5 further comprising separating the liquid composition from the formylation, ketalization, or halogenation product mixtures by including in the formylation, ketalization, or halogenation product mixtures a water soluble solvent having a boiling point that is greater than the boiling point of the liquid composition, and heating the formylation, ketalization, or halogenation product mixtures to a temperature in excess of the boiling point of the liquid composition to remove the liquid composition and leave the N-formyl derivative (900), the ketal (1000), or the haloketal (1100) dissolved in the water soluble solvent.

8. The process of claim 4 further comprising converting the haloketal (1100) to a haloketone (1200) with a hydrolyzing agent, whereby the conversion of the haloketal (1100) to the haloketone (1200) proceeds without an intermediate crystallization of the haloketal (1100); wherein the haloketone (1200) corresponds to Formula (1200):

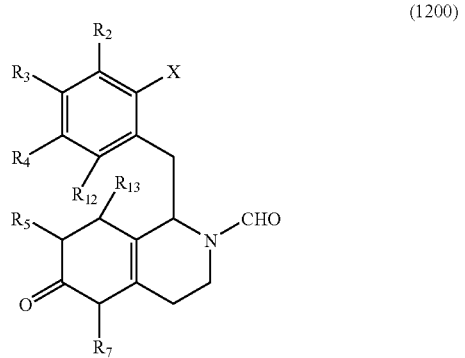

(1200)

$R_2$ is hydrogen, hydrocarbyl, substituted hydrocarbyl, halo, or $—OR_{211}$;

$R_3$ is hydrogen, hydrocarbyl, substituted hydrocarbyl, or $—OR_{311}$;

$R_4$ is hydrogen, hydrocarbyl, substituted hydrocarbyl, halo, or $—OR_{411}$;

$R_5$ is hydrogen, hydrocarbyl, substituted hydrocarbyl, or $—OR_{511}$;

$R_7$ is hydrogen, hydrocarbyl, substituted hydrocarbyl, or $—OR_{111}$;

$R_{12}$ is hydrogen, hydrocarbyl, substituted hydrocarbyl, halo, or $—OR_{121}$;

$R_{13}$ is hydrogen, hydrocarbyl, substituted hydrocarbyl, halo, or $—OR_{511}$;

$R_{111}$ is hydrogen, hydrocarbyl, substituted hydrocarbyl, or a hydroxy protecting group;

$R_{121}$ is hydrogen, hydrocarbyl, or substituted hydrocarbyl;

$R_{211}$ is hydrogen, hydrocarbyl, substituted hydrocarbyl, or a hydroxy protecting group;

$R_{311}$ is hydrogen, hydrocarbyl, substituted hydrocarbyl, or a hydroxy protecting group;

$R_{411}$ is hydrogen, hydrocarbyl, substituted hydrocarbyl, or a hydroxy protecting group;

$R_{511}$ is hydrogen, hydrocarbyl, substituted hydrocarbyl, or a hydroxy protecting group; and X is halo.

9. The process of claim 7 wherein the conversion of the N-formyl derivative (900) to the ketal (1000), the ketal (1000) to the haloketal (1100), or the haloketal (1100) to the haloketone (1200) further comprises separating the N-formyl derivative (900), the ketal (1000), or the haloketal (1100) from the water soluble solvent by (i) combining the N-formyl derivative (900), the ketal (1000), or the haloketal (1100) and the water soluble solvent with a water immiscible solvent and an aqueous solution comprising water to form an extraction mixture comprising (A) a water immiscible solvent portion comprising the N-formyl derivative (900), the ketal (1000), or the haloketal (1100) dissolved in the water immiscible solvent, and (B) an aqueous portion comprising solubilized water soluble solvent, and (ii) separating the water immiscible solvent portion from the extraction mixture.

10. The process of claim 8 further comprising converting the haloketone (1200) to a morphinan-6-one (1300) with a cyclizing acid and an acid anhydride, whereby the conversion of the halo ketone (1200) to the morphinan-6-one (1300) proceeds without an intermediate cyclization of the halo ketone (1200); wherein the morphinan-6-one corresponds to Formula (1300):

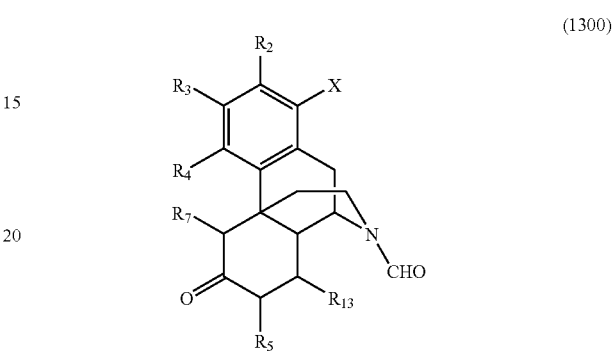

(1300)

$R_2$ is hydrogen, hydrocarbyl, substituted hydrocarbyl, halo, or $—OR_{211}$;

$R_3$ is hydrogen, hydrocarbyl, substituted hydrocarbyl, or $—OR_{311}$;

$R_4$ is hydrogen, hydrocarbyl, substituted hydrocarbyl, halo, or $—OR_{411}$;

$R_5$ is hydrogen, hydrocarbyl substituted hydrocarbyl, or $—OR_{511}$;

$R_7$ is hydrogen, hydrocarbyl, substituted hydrocarbyl, or $—OR_{111}$;

$R_{13}$ is hydrogen, hydrocarbyl, substituted hydrocarbyl, halo, or $—OR_{511}$;

$R_{111}$ is hydrogen, hydrocarbyl, substituted hydrocarbyl, or a hydroxy protecting group;

$R_{211}$ is hydrogen, hydrocarbyl, substituted hydrocarbyl, or a hydroxy protecting group;

$R_{311}$ is hydrogen, hydrocarbyl, substituted hydrocarbyl, or a hydroxy protecting group;

$R_{411}$ is hydrogen, hydrocarbyl, substituted hydrocarbyl, or a hydroxy protecting group;

$R_{511}$ is hydrogen, hydrocarbyl, substituted hydrocarbyl, or a hydroxy protecting group; and X is halo.

11. The process of claim 10 wherein the conversion of the haloketone (1200) to the morphinan-6-one (1300) proceeds in the presence of a water immiscible solvent.

12. The process of claim 11 wherein the conversion of the haloketone (1200) to the morphinan-6-one (1300) proceeds by treating the halogenation product mixture with the cyclizing acid to form the cyclization product mixture containing the morphinan-6-one (1300) in the water immiscible solvent.

13. The process of claim 12 further comprising treating the cyclization product mixture containing the morphinan-6-one (1300) with an acid or base salt to form a morphinan-6-one salt product mixture containing a morphinan-6-one salt (1400); wherein the morphinan-6-one salt (1400) corresponds to Formula (1400):

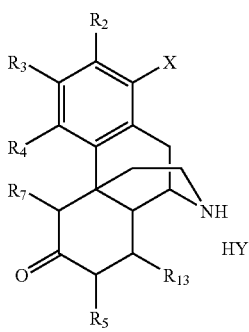

(1400)

R₂ is hydrogen, hydrocarbyl, substituted hydrocarbyl, halo, or —OR₂₁₁;
R₃ is hydrogen, hydrocarbyl, substituted hydrocarbyl, or —OR₃₁₁;
R₄ is hydrogen, hydrocarbyl, substituted hydrocarbyl, halo, or —OR₄₁₁;
R₅ is hydrogen, hydrocarbyl, substituted hydrocarbyl, or —OR₅₁₁;
R₇ is hydrogen, hydrocarbyl, substituted hydrocarbyl, or —OR₁₁₁;
R₁₃ is hydrogen, hydrocarbyl, substituted hydrocarbyl, halo, or —OR₅₁₁;
R₁₁₁ is hydrogen, hydrocarbyl, or substituted hydrocarbyl;
R₁₂₁ is hydrogen, hydrocarbyl, or substituted hydrocarbyl;
R₂₁₁ is hydrogen, hydrocarbyl or substituted hydrocarbyl;
R₃₁₁ is hydrogen, hydrocarbyl or substituted hydrocarbyl;
R₄₁₁ is hydrogen, hydrocarbyl or substituted hydrocarbyl;
R₅₁₁ is hydrogen, hydrocarbyl, or substituted hydrocarbyl;
X is halo; and
Y is a counterion.

14. The process of claim 1 wherein the formylating agent is formic acid, propyl formate, or butyl formate.

15. The process of claim 1 wherein the formylation product mixture is heated to a temperature of at least about 70° C.

16. The process of claim 4 wherein the conversion of the N-formyl derivative (900) to the ketal (1000) proceeds in the presence of a water scavenger.

17. The process of claim 4 wherein the conversion of the ketal (1000) to the haloketal (1100) proceeds in the presence of a water scavenger.

18. The process of claim 4 wherein the conversion of the N-formyl derivative (900) to the ketal (1000) and the conversion of the ketal (1000) to the haloketal (1100) each proceed in the presence of a water scavenger.

19. The process of claim 18 wherein the water scavenger corresponds to the formula: $R_YC(OR_Z)_3$, wherein $R_Y$ is hydrogen or hydrocarbyl and $R_Z$ is hydrocarbyl.

20. The process of claim 1 wherein the ketalizing agent is selected from the group consisting of alkanols, alkanediols, and thiols.

21. The process of claim 4 wherein the halogenating agent is selected from the group consisting of chlorine ($Cl_2$), bromine ($Br_2$), N-bromoacetamide (NBA), N-bromosuccinimide (NBS), 1,3-dibromo-5,5-methylhydantoin (OBDMH), 1,3-dichloro-5,5-methylhydantoin (DCDMH), N-chlorosuccinimide (NCS), pyridinium tribromide, and combinations thereof.

22. The process of claim 8 wherein the hydrolyzing agent is selected from the group consisting acetic acid, oxalic acid, formic acid, propanoic acid, butanoic acid, pentanoic acid, benzoic acid, hydrochloric acid, sulfuric acid, methanesulfonic acid, hydrobromic acid, trifluoroacetic acid, and combinations thereof.

23. The process of claim 2 wherein the solvent is selected from the group consisting of chlorobenzene, toluene, butyl acetate, dimethoxyethane, acetonitrile, 1,2-dichloroethane, 1,4-dioxane, ethyl acetate, propyl acetate, ethanol, 1-butanol, 2-butanol, 1-propanol, 2-propanol, tert-butanol, acetic acid, 2-methoxyethanol, and combinations thereof.

24. The process of claim 7 wherein the water soluble solvent is selected from the group consisting of dimethylformamide (DMF), dimethylsulfoxide (DMSO), dimethylacetamide (DMAC), N-methylpyrrolidinone (NMP), 1,2-ethanediol, isopropanol, isobutanol, tert-butanol, and n-butanol.

25. The process of claim 10 wherein the cyclizing acid comprises a strong acid, a super acid, and combinations thereof.

26. The process of claim 1 wherein R₂ is hydrogen or —OR₂₁₁; and R₂₁₁ is hydrogen, alkyl, acyl, alkaryl, aryl, or a hydroxyl protecting group.

27. The process of claim 26 wherein R₃ is hydrogen or —OR₃₁₁; and R₃₁₁ is hydrogen, alkyl, acyl, alkaryl, aryl, or a hydroxyl protecting group.

28. The process of claim 27 wherein R₄ is hydrogen or —OR₄₁₁; and R₄₁₁ is hydrogen, alkyl, acyl, alkaryl, aryl, or a hydroxyl protecting group.

29. The process of claim 1 wherein R₂ is hydrogen; R₃ is —OR₃₁₁; R₄ is —OR₄₁₁; R₃₁₁ is alkyl; and R₄₁₁ is hydrogen.

30. The process of claim 29 wherein R₁, R₅, R₇, R₁₂, and R₁₃ are hydrogen.

31. The process of claim 4 wherein X is bromo.

* * * * *